(12) United States Patent
Del Corso

(10) Patent No.: US 9,332,975 B2
(45) Date of Patent: May 10, 2016

(54) OCCLUSION DEVICE FOR VASCULAR SURGERY

(76) Inventor: Andrea Del Corso, Villa Basilica (IT)

( * ) Notice: Subject to any disclaimer, the term of this patent is extended or adjusted under 35 U.S.C. 154(b) by 342 days.

(21) Appl. No.: 13/058,870

(22) PCT Filed: Aug. 13, 2009

(86) PCT No.: PCT/IB2009/006529
§ 371 (c)(1),
(2), (4) Date: Mar. 24, 2011

(87) PCT Pub. No.: WO2010/018447
PCT Pub. Date: Feb. 18, 2010

(65) Prior Publication Data
US 2011/0178399 A1    Jul. 21, 2011

(30) Foreign Application Priority Data

Aug. 13, 2008 (IT) .................. PI2008A0076
Feb. 20, 2009 (IT) .................. PI2009A0016

(51) Int. Cl.
*A61B 17/03* (2006.01)
*A61M 37/00* (2006.01)
*A61B 6/00* (2006.01)
*A61B 17/00* (2006.01)

(52) U.S. Cl.
CPC ....... *A61B 17/0057* (2013.01); *A61B 17/00491* (2013.01); *A61B 2017/0065* (2013.01); *A61B 2017/00292* (2013.01); *A61B 2017/00575* (2013.01)

(58) Field of Classification Search
CPC .............. A61B 17/00491; A61B 17/0057; A61B 2017/00292; A61B 2017/00575; A61B 2017/0065
See application file for complete search history.

(56) References Cited

U.S. PATENT DOCUMENTS

| | | | | |
|---|---|---|---|---|
| 3,548,825 A * | 12/1970 | Shaw | ............... | 604/91 |
| 4,402,319 A * | 9/1983 | Handa et al. | ............ | 606/195 |
| 4,838,280 A * | 6/1989 | Haaga | ............... | 600/564 |
| 4,941,475 A * | 7/1990 | Williams et al. | ............ | 600/505 |
| 5,292,332 A * | 3/1994 | Lee | ............... | 606/213 |
| 5,447,502 A * | 9/1995 | Haaga | ............... | 604/265 |
| 5,486,195 A * | 1/1996 | Myers et al. | ............ | 606/213 |
| 5,527,292 A * | 6/1996 | Adams et al. | ............ | 604/171 |
| 5,649,959 A * | 7/1997 | Hannam et al. | ............ | 606/213 |
| 5,725,551 A * | 3/1998 | Myers et al. | ............ | 606/213 |

(Continued)

FOREIGN PATENT DOCUMENTS

| | | |
|---|---|---|
| WO | 02089675 | 11/2002 |
| WO | 2006066336 | 6/2006 |

*Primary Examiner* — Michael Rozanski
(74) *Attorney, Agent, or Firm* — Ladas & Parry LLP

(57) ABSTRACT

An occlusion device for vascular surgery, suitable for clogging treatments of vascular entry sites and for endovascular interventions such as embolizations of blood vessels, treatment of arteriovenous malformations or small aneurysms, arterial dissections and the like, by releasing in an operation region a quick setting surgical glue or haemostatic fluid, through an outlet mouth of a duct. The device prevents the surgical glue from contacting within the duct a patient's biological fluids, in particular blood, which would close the duct. In the case of clogging treatments of vascular entry sites, a backflow preventing device may be provided, preferably provided by a coupling device between the duct and an introducer sheath by which an outlet mouth is kept in contact to keep in a one-way fluid tight contact against the outer surface of the introducer sheath until an injection pressure P2 is applied to cause release of the surgical glue.

23 Claims, 17 Drawing Sheets

(56) References Cited

U.S. PATENT DOCUMENTS

| | | | |
|---|---|---|---|
| 5,728,132 A * | 3/1998 | Van Tassel et al. | 606/213 |
| 5,772,639 A * | 6/1998 | Lampropoulos et al. | 604/264 |
| 5,797,886 A * | 8/1998 | Roth et al. | 604/264 |
| 5,817,072 A * | 10/1998 | Lampropoulos et al. | 604/264 |
| 5,843,051 A * | 12/1998 | Adams et al. | 604/525 |
| 5,938,645 A * | 8/1999 | Gordon | 604/264 |
| 6,033,401 A * | 3/2000 | Edwards et al. | 606/41 |
| 6,090,072 A * | 7/2000 | Kratoska et al. | 604/164.01 |
| 6,121,341 A * | 9/2000 | Sawhney et al. | 522/84 |
| 6,159,232 A * | 12/2000 | Nowakowski | 606/213 |
| 6,245,083 B1 * | 6/2001 | Black et al. | 606/153 |
| 6,306,154 B1 * | 10/2001 | Hudson et al. | 606/196 |
| 6,387,977 B1 * | 5/2002 | Sawhney et al. | 522/184 |
| 6,398,756 B2 * | 6/2002 | Peterson et al. | 604/96.01 |
| 6,478,808 B2 * | 11/2002 | Nowakowski | 606/213 |
| 6,482,179 B1 * | 11/2002 | Chu et al. | 604/164.09 |
| 6,482,223 B1 * | 11/2002 | Nowakowski et al. | 606/213 |
| 6,524,326 B1 * | 2/2003 | Zhu et al. | 606/213 |
| 6,562,059 B2 * | 5/2003 | Edwards et al. | 606/213 |
| 6,629,947 B1 * | 10/2003 | Sahatjian et al. | 604/13 |
| 6,733,515 B1 * | 5/2004 | Edwards et al. | 606/214 |
| 6,764,461 B2 * | 7/2004 | Mickley et al. | 604/15 |
| 6,818,008 B1 * | 11/2004 | Cates et al. | 606/213 |
| 6,989,022 B2 * | 1/2006 | Nowakowski | 606/213 |
| 7,029,489 B1 * | 4/2006 | Ashby et al. | 606/213 |
| 7,037,322 B1 * | 5/2006 | Sing et al. | 606/213 |
| 7,493,154 B2 * | 2/2009 | Bonner et al. | 600/424 |
| 7,505,812 B1 * | 3/2009 | Eggers et al. | 604/20 |
| 7,625,352 B1 * | 12/2009 | Ashby et al. | 604/15 |
| 7,722,579 B2 * | 5/2010 | Collins et al. | 604/264 |
| 7,842,026 B2 * | 11/2010 | Cahill et al. | 604/533 |
| 7,931,637 B2 * | 4/2011 | Vournakis et al. | 604/389 |
| 7,955,305 B2 * | 6/2011 | Moberg et al. | 604/164.01 |
| 8,221,452 B2 * | 7/2012 | Edwards et al. | 606/214 |
| 8,263,223 B2 * | 9/2012 | Ericson et al. | 428/406 |
| 8,308,681 B2 * | 11/2012 | Slocum et al. | 604/82 |
| 8,652,168 B2 * | 2/2014 | Nowakowski | 606/214 |
| 8,752,552 B2 * | 6/2014 | Nelson et al. | 128/848 |
| 2001/0001316 A1 * | 5/2001 | Nowakowski | 606/214 |
| 2001/0031948 A1 * | 10/2001 | Cruise et al. | 604/191 |
| 2001/0031982 A1 * | 10/2001 | Peterson et al. | 606/200 |
| 2002/0006429 A1 * | 1/2002 | Redmond et al. | 424/425 |
| 2002/0055712 A1 * | 5/2002 | Neracher | 604/143 |
| 2002/0058960 A1 * | 5/2002 | Hudson et al. | 606/192 |
| 2002/0062104 A1 * | 5/2002 | Ashby et al. | 604/93.01 |
| 2002/0169391 A1 * | 11/2002 | Hung et al. | 600/562 |
| 2003/0009194 A1 * | 1/2003 | Saker et al. | 606/213 |
| 2003/0069601 A1 * | 4/2003 | Nowakowski et al. | 606/214 |
| 2003/0088269 A1 * | 5/2003 | Ashby | 606/213 |
| 2003/0093116 A1 * | 5/2003 | Nowakowski | 606/215 |
| 2003/0212394 A1 * | 11/2003 | Pearson et al. | 606/41 |
| 2003/0216695 A1 * | 11/2003 | Yang | 604/200 |
| 2003/0225378 A1 * | 12/2003 | Wilkie et al. | 604/221 |
| 2003/0225380 A1 * | 12/2003 | Redl et al. | 604/289 |
| 2003/0229376 A1 * | 12/2003 | Sandhu | 606/214 |
| 2003/0236573 A1 * | 12/2003 | Evans et al. | 623/23.58 |
| 2004/0019328 A1 * | 1/2004 | Sing et al. | 604/164.02 |
| 2004/0019330 A1 * | 1/2004 | Ashby | 604/168.01 |
| 2004/0167473 A1 * | 8/2004 | Moenning | 604/164.02 |
| 2004/0167478 A1 * | 8/2004 | Mooney et al. | 604/264 |
| 2004/0176723 A1 * | 9/2004 | Sing et al. | 604/131 |
| 2004/0220562 A1 * | 11/2004 | Garabedian et al. | 606/41 |
| 2005/0033360 A1 * | 2/2005 | Sing et al. | 606/213 |
| 2005/0049691 A1 * | 3/2005 | Mericle et al. | 623/1.23 |
| 2005/0107738 A1 * | 5/2005 | Slater et al. | 604/96.01 |
| 2005/0107826 A1 * | 5/2005 | Zhu et al. | 606/213 |
| 2005/0113798 A1 * | 5/2005 | Slater et al. | 604/508 |
| 2005/0182071 A1 * | 8/2005 | Seward et al. | 514/255.06 |
| 2005/0245862 A1 * | 11/2005 | Seward et al. | 604/95.04 |
| 2005/0245876 A1 * | 11/2005 | Khosravi et al. | 604/164.1 |
| 2006/0149218 A1 * | 7/2006 | Slater et al. | 604/509 |
| 2006/0161110 A1 * | 7/2006 | Lenker et al. | 604/183 |
| 2006/0178610 A1 * | 8/2006 | Nowakowski | 604/4.01 |
| 2006/0253072 A1 * | 11/2006 | Pai et al. | 604/104 |
| 2007/0021768 A1 * | 1/2007 | Nance et al. | 606/192 |
| 2007/0060950 A1 * | 3/2007 | Khosravi et al. | 606/213 |
| 2007/0123816 A1 * | 5/2007 | Zhu et al. | 604/57 |
| 2008/0015625 A1 * | 1/2008 | Ventura et al. | 606/191 |
| 2008/0058650 A1 * | 3/2008 | Saadat et al. | 600/478 |
| 2008/0097509 A1 * | 4/2008 | Beyar et al. | 606/192 |
| 2008/0105700 A1 * | 5/2008 | Voegele et al. | 222/1 |
| 2009/0099515 A1 * | 4/2009 | Quilter | 604/96.01 |
| 2009/0124996 A1 * | 5/2009 | Heneveld et al. | 604/506 |
| 2009/0143765 A1 * | 6/2009 | Slocum et al. | 604/518 |
| 2009/0171282 A1 * | 7/2009 | Pipenhagen et al. | 604/103.01 |
| 2009/0171387 A1 * | 7/2009 | Pipenhagen et al. | 606/213 |
| 2010/0274279 A1 * | 10/2010 | Delmotte | 606/213 |
| 2011/0295226 A1 * | 12/2011 | Shohat et al. | 604/500 |

* cited by examiner

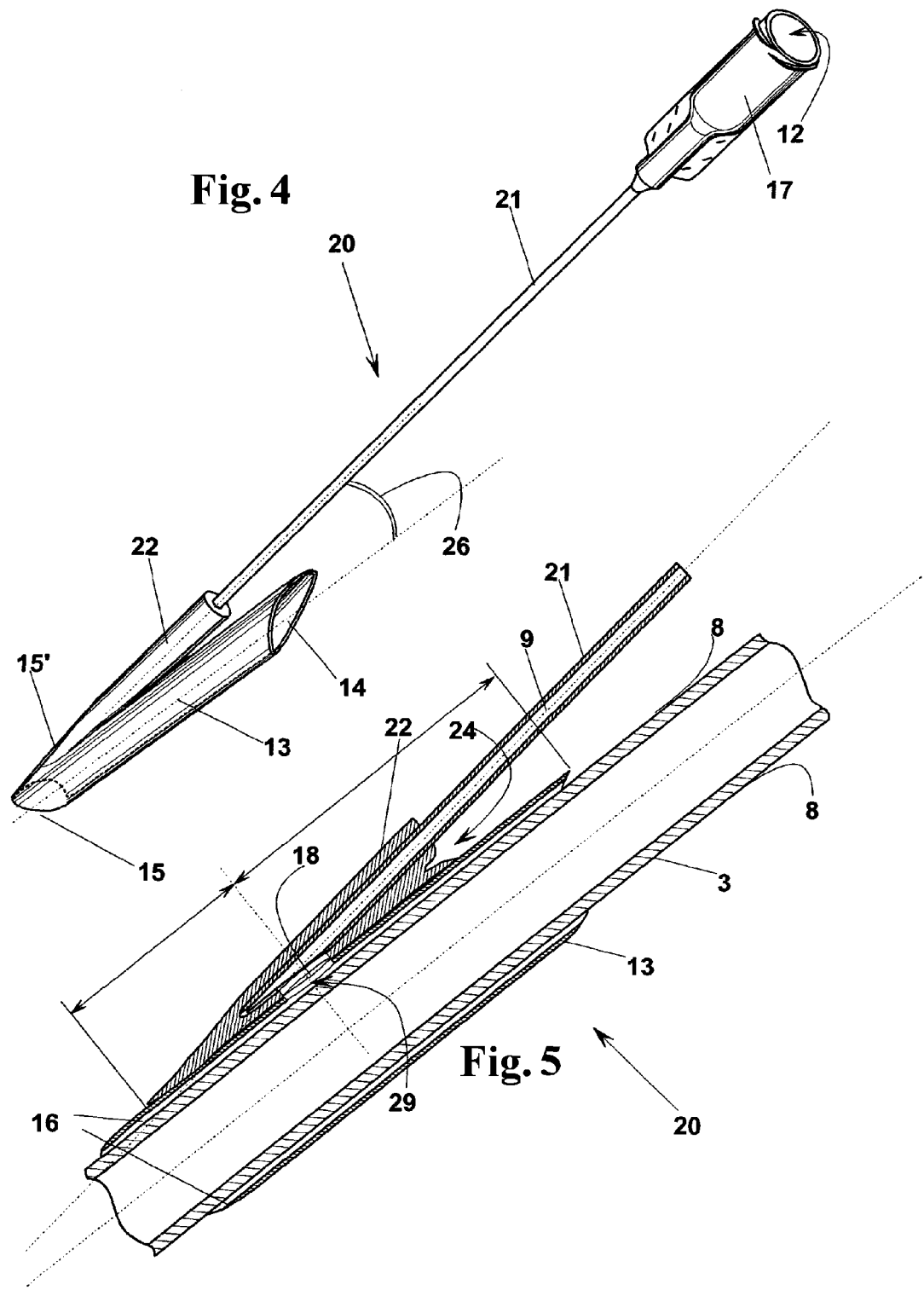

A-A

A-A

A - A

A - A

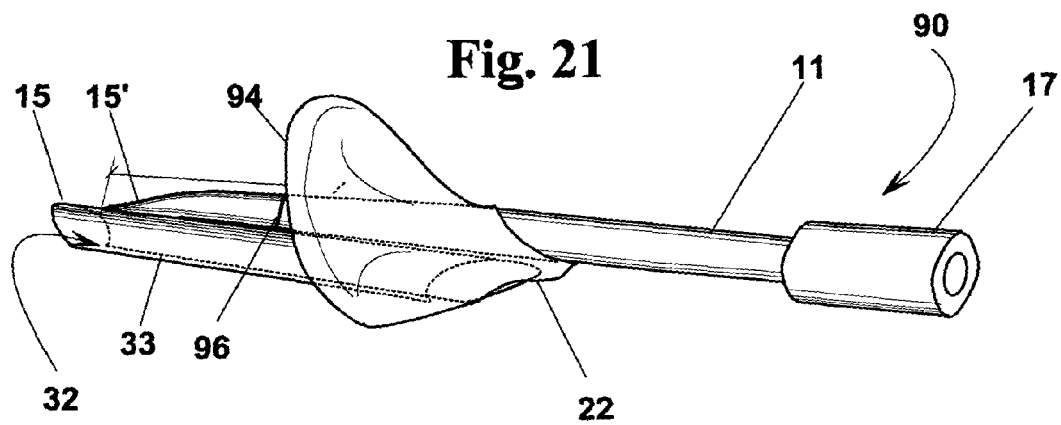

OCCLUSION DEVICE FOR VASCULAR SURGERY

FIELD OF THE INVENTION

The present invention relates to a device for percutaneously closing apertures in walls of blood vessels and vascular prosthesis. Such apertures are made to perform diagnostic examinations, or to position surgical instruments for endovascular interventions. The invention relates also to a device for treating blood vessels haemorrhagic, dilatative or dissecting pathologies or arteriovenous malformations.

In particular, the device can be used at the end of such a diagnostic procedure as arteriography or coronarography, or of such an endovascular intervention as angioplasty, stenting or embolization, which require a percutaneous puncture of an artery for positioning an introducer sheath in the vascular bed. In specific exemplary embodiments, the device can be used for treating pseudoaneurysms, for arterials or venous embolization, or for treating dissections of arterial walls.

BACKGROUND OF THE INVENTION

Many diagnostic and therapeutic procedures provide the step of percutaneously introducing instruments and/or catheters through vascular entry sites. To this purpose, introducer sheaths are used, i.e. substantially cylindrical valved cannulas, which are removed only at the end of the procedure.

At the moment of the removal of the introducer sheath, the entry site, i.e. a hole in the wall of the artery, remains open and must be immediately closed to avoid bleeding. For closing the hole and stopping the blood outflow at the removal of the introducer sheath, a well-known technique provides exerting a compression force at the entry site, first manually and then by means of a bandage or by application of a weight. The compression force causes also a local reduction of the arterial blood pressure proximate to the entry site, which first allows natural haemostasis process to start, and which then avoids that sudden blood pressure changes or movements of the patient causes the entry site to open again. Once bleeding has been stopped, the repair of the entry site is completed within a few days. For instance, in the case of a femoral entry site of a patient who has normal coagulation parameters, the closing treatment of the entry site by a means of compression usually lasts between 8 and 12 hours, during which the patient must remain motionless.

Complications may sometimes arise such as bleeding, hematomas, pseudoaneurysms, in particular in the case of patients whose blood hardly coagulate due to a disease or to an a anticoagulation treatment, or in the case of patients who have a vascular prosthesis (by-pass) at the inguinal region.

In some cases, even by prolonging the compression the entry site cannot be closed, and a surgical treatment is necessary, which may involve further risks, discomfort, prolonged period in bed and resources waste. Furthermore, in case of obese patients, the adipose layer that is located between the skin and the vascular entry site reduces the efficiency of the compression.

Moreover, an entry site on a vascular prosthesis that is made of plastic (Dacron, PTFE, etc.) cannot heal by the natural repair processes of an artery, and, on the contrary, it can only be closed by formation of a true plug made of blood that, after flowing out of the opening, coagulates through the tissues that surround the prosthesis, under the assistance of the compression force. In this case, therefore, the risk that bleeding may start again when the compression force is released is much higher, which suggests to avoid entry sites of vascular prosthesis; on the other hand, this is particularly desirable when dilatative or stenosing diseases have to be solved upstream or downstream of the prosthesis.

Systems are also known for closing percutaneous entry sites, which comprise a suture means and/or a mechanical closing means, such as grafts or plaques, which may be associated with a haemostatic liquid. Such systems reduce the average treatment time. However, the introduction of objects into the blood vessels may cause thrombosis related ischemia, embolism, arterial wall laceration, sensitization, allergic reaction. Furthermore, the mechanical closure devices require a highly skilled operator, and/or the work of further assistant operators. Therefore, these techniques do not provide a valid alternative to the traditional techniques.

Systems are also known for closing the entry site of an introducer sheath with exclusive use of a haemostatic liquid, in particular collagen, to form clots that are involved in a natural coagulation mechanisms; however, the haemostasis process is slow, and complications may arise such as blood suffusion, bleeding, pseudoaneurysms.

Quickly setting haemostatic liquids are also known, which would be well-suited for forming a strong and flexible closure at the entry site. Liquid of this kind, such as internal use surgical glues, have not been used so far for closing percutaneous vascular entry sites, since:

- for injecting a haemostatic liquid in a narrow space like that is available at a percutaneous access, it is preferable to use small cross section ducts, to limit the amount of liquid to be used and to avoid the production of hardened lumps under the skin; similar ducts are easily closed by the quickly-setting haemostatic liquids that quickly harden by reacting with blood, lymph or other biological material that enters the duct during the puncture, which makes the injection impossible to carry out;
- it is very difficult to release a quick setting haemostatic liquid in a pure state in an operation region where blood under pressure is present. The methods that use quick setting surgical glues provide a dilution of the glue, but this prolongs the hardening time;
- with well known techniques, and also under echographic control, it is difficult to release such pure quick setting haemostatic liquid proximate to a vascular entry site without the risk of injecting it into the blood vessel, with such complications as thrombosis or embolisms. For this reason, in order to use a quick setting haemostatic liquid, and at the same time to avoid an echographic control, it is important to establish as precisely as possible the position of the point where the liquid must be released.

The echographic control may not be always available when this kind of intervention is performed, because it requires experienced operators and in any case it requires more than one operator for closing the entry site.

To this purpose, in EP0941697 a device is described for bringing a haemostatic substance proximate to a percutaneous entry site. The device comprises a cylindrical body that is coaxially coupled to the introducer sheath that slides along it until a "sensation" is felt that the device has reached the artery. Then the haemostatic substance is released. The device is mounted on the introducer sheath before positioning it in the blood vessel; therefore, it prevents the use of the whole length of the introducer sheath, which obliges a portion of the introducer sheath to be left outside of the skin, differently from what happens in the normal procedure. This causes an unsteady positioning of the introducer sheath, which is particularly critical in the case of obese patients, where the distance between the skin and the blood vessel is higher than in normal patients. Furthermore, the large transversal size of the device hinders the movement through the tissues, and "digs" an enlarged space about the introducer sheath in which both the released haemostatic liquid and the blood can accumulate without contributing to the entry site occlusion. In any case, the device is not adapted to treat a quick-setting liquid, because the delivery mouth may be easily clogged.

Various systems have been proposed to provide a liquid that is adapted is to make an occlusion in an operation region.

In particular the device of US2008/45700 is adapted to treat bleeding diseases, for example, in the stomach and in the intestine, but it cannot be used neither for an endovascular intervention, nor for closing an arterial entry site. Due to its high reactivity, a cyanoacrylate material would immediately polymerize when brought into contact with the blood, which would reduce the passage through the catheter, or even clog it, in such a way that the release of a significant amount of surgical glue would be impossible.

US patent application 2001/000616 relates to a method for applying a blood-based pro-coagulating substance proximate to a vascular entry site through a hole of a catheter to be inserted through an introducer sheath. For positioning the hole immediately out of the artery, the operator slowly withdraws the catheter until the blood stops flowing out of the distal end of it. This is a rough method, by which the risk may arise of injecting the procoagulating substance into the vessel; for the same reason, the method and the apparatus cannot be used to safely release surgical glues, which are not cited in the patent application.

International patent application WO 02/089675 relates to a device and to a method for blocking an arterial entry site of a patient who has been treated with anticoagulant therapy. This invention relates however to the use of blood that is taken from the patient itself and is treated with a substance that is an antagonists of the anticoagulant treatment, whereas it does not deal with surgical glues or similar liquids. Furthermore, the document does not provide precise indications about the way the liquid is supplied at the entry site. In any case, the device cannot be used to release a quick setting surgical glue proximate to an entry site, because the glue would come into contact too early with the nearby biological fluids which would block the device; furthermore, it does not allow an operator to determine the point of delivery, unless an echographic control is provided.

U.S. Pat. No. 3,548,825 relates to a syringe for injecting a mixture of two components that are contained in respective receptacles of the syringe, which allows mixing the liquids at the moment of the injection. Similarly to any well-known syringe, a similar device does not allow providing a quick setting. in particular of a haemostatic liquid in a pure state, at an entry site or in an is operation region of an endovascular surgery.

Concerning the endovascular surgery, such as an embolization of arterial or venous districts, or the treatment of arterial walls dissections, the problem often arises of covering a long distance between the entry site, which is normally made in the artery of the arm or in the femoral artery, and the operation region. When the use is desirable of a pure quick setting surgical glue, which would have a maximum efficiency and application speed, the problem arises of conveying the glue through a long duct, and of preventing at the same time any risks of contact between the glue and the blood until the remote vascular district is reached where the intervention must be made.

SUMMARY OF THE INVENTION

It is therefore an object of the present invention to provide an occlusion device for haemostasis of arterial entry sites and for endovascular treatment, which uses a quick setting haemostatic liquid, for example a surgical glue, preventing the haemostatic liquid from prematurely hardening in the device and causing it to block.

It is, furthermore, an object of the present invention to provide a device for releasing such a liquid at an operation region in a pure, i.e. undiluted state.

It is a particular object of the present invention to provide such a device for bringing this liquid close to an arterial entry site for occluding the opening that results from the extraction of an introducer sheath, stopping the bleeding after the extraction of a catheter introducer sheath.

It is a particular object of the present invention to provide such a device that prevents such a liquid from flowing into an artery through the opening, without using echographic or radiographic control means.

It is still a particular object of the present invention to provide such a device for closing percutaneous entry sites of vascular prosthesis, in particular, of by-pass prosthesis made of Dacron or of PTFE.

It is another particular object of the present invention to provide such a device for bringing such a liquid to a prefixed vascular district for carrying out an endovascular intervention without modifying the quick hardening properties of the liquid, assuring therefore a complete reaction, and limiting the possibility of spreading in vascular remote districts.

It is another object of the present invention to provide such a device that encounters a minimum resistance while crossing tissues to reach the point of release of the liquid in a procedure of occlusion of a vascular entry site, using as far as possible a channel formed around the introducer sheath.

It is also an object of the present invention to provide such a device that can be easily handled by an operator.

These and other objects are achieved by a device for causing a release of a surgical glue in an operation region in a patient's body for blocking a flow of blood of an artery, the device comprising a duct having an inlet port and an outlet mouth for said surgical glue, said duct adapted to move through a biological medium in the patient's body from an opening on a skin plane of said patient to said operation region in such a way that, once said operation region has been reached by said duct, said outlet mouth is in said operation region and said inlet port remains outside of said opening in said skin plane, said inlet port in use hydraulically connected with a source of said surgical glue and with a pressurizing means that can be operated by an operator for applying an injection pressure on said surgical glue and for causing:

an outflow of said surgical glue through said duct, and
said release of surgical glue at said operation region through said outlet mouth, the main feature of the device is that a liquid contact preventing means is provided that is associated to said duct, said liquid contact preventing means adapted to impede in said duct a contact of said surgical glue with said biological medium before said outflow, in particular a contact of said surgical glue with blood of said patient.

This way, the liquid contact preventing means does not allow that the blood, or other biological material coming from the operation region, can penetrate into the duct and interact with the surgical glue before the injection. In fact, such penetration would cause the inconvenience of a premature hardening of the surgical glue inside the duct, which would immediately clog the duct and would make the release impossible. The present invention allows therefore the use of surgical glues that are particularly reactive with blood and with other biological fluids, such as cyanoacrylic glues, which can be easily transferred into the operation region in an undiluted state. Such highly reactive glues are well-suited for internal use, but their application is presently limited by the above-described drawbacks.

In particular, said liquid contact preventing means comprises a backflow preventing means that is adapted to prevent a material of said biological medium from penetrating into said duct.

In particular, a coupling means is provided which is adapted to couple said duct with an elongated introducer sheath that can extend in use between said opening on said skin plane and a vascular entry site, said introducer sheath having an outer surface, and said coupling means adapted to engage in use with the outer surface of said introducer sheath. This way, when the operation region is a neighbourhood of an arterial entry site, or of an entry site of a vascular prosthesis, which is engaged by an introducer sheath, the invention allows immediately to block bleeding when said introducer sheath is withdrawn from said entry site, and said surgical glue is at the same time injected onto said introducer sheath from said outlet mouth. In fact, due to said coupling means, said outlet mouth is in a close proximity of said introducer sheath. Therefore, by extracting the introducer sheath from the entry site, together with the device, a channel is left free, which is filled with the surgical glue, preferably under the action of a manual compression exerted on the skin, which cleans the introducer sheath during the extraction, and causes the glue to remain immediately outside the entry site.

In particular, said outlet mouth is arranged between said duct and said outer surface of said introducer sheath, and said backflow preventing means is provided by said coupling means, said coupling means suitable for keeping said outlet mouth in a one-way fluid tight contact against said outer surface of said introducer sheath, such that said outlet mouth detaches from said introducer sheath only when said pressurizing means is operated. In other words, a backflow preventing means may be provided by the coupling means itself, which is made in such a way that the outlet mouth is kept tight against the introducer sheath, such that the introducer sheath keeps the outlet mouth closed until an injection pressure is created by the operator.

Advantageously, said coupling means is a sliding coupling means, i.e. it comprises a slide portion of said duct associated with a driving portion of said introducer sheath.

For example, the driving portion is a groove along which the duct slides, the duct having a shape suitable for firmly engaging with the groove. Advantageously, the groove has an undercut portion with which the duct firmly engages. In alternative, the driving portion is a protrusion of the introducer sheath, and the slide portion is a groove with a shape that corresponds with the protrusion.

Advantageously, said coupling means comprises a short tube that is coaxially coupled with said elongated introducer sheath. In this case, the driving portion is the introducer sheath itself, which is substantially cylindrical, and the slide portion is the short tube itself.

Preferably, the short tube has a thickness that is set between 40 and 300 micron, in particular, between 40 and 70 micron. Advantageously, the duct has a tapering surface at the outlet mouth, such that its transversal size decreases along the front portion, i.e. along the portion that in use is arranged most proximate to the entry site. In particular, a smooth connection is provided within the duct and the short tube, in order to create a minimum resistance. Preferably, the duct extends along the short tube, and a front portion of the short tube is left free from the duct, said front portion having a length that is preferably set between 2 and 4 mm. Such features of the short tube and of the duct, separately considered, assist the movement through the tissues between the skin plane and the operation region, in particular the small thickness of the short tube allows using the zone of the tissues that surrounds the introducer sheath, which is already modified by the introducer itself, and where the resistance to the forward movement of the short tube is lowest.

In alternative, said outlet mouth is laterally arranged with respect to said duct. This way, it is possible to move the duct through the tissues without any risk of clotting the outlet mouth.

Preferably, said outlet mouth and said short tube are such that said surgical glue is released in an annular narrow space that is defined between said short tube and said introducer sheath, such that said surgical glue reaches said operation region through said annular narrow space. In these conditions, the surgical glue works in two ways:
    as already described, in a portion of a channel that is most proximate to the entry site, it interacts with the blood that flows out of the entry site, thus stopping the bleeding;
    in the portions of the channel that are more distant from the entry site, it engages mainly with such other biological materials as fat, lymph, periadventitial tissues, sticking together the walls of the channel and sealing the channel.

As already said, the operation region is a region between the skin and the entry site of the blood vessel, where the biological tissues have been modified by the introduction and by the permanence of the introducer sheath. The surgical glue, in particular a low viscosity one, tends naturally to flow inside this lower resistance region, about the introducer sheath. In this case, the short tube advantageously assists the release of the surgical glue on the introducer sheath itself in such a way that, when the introducer is withdrawn, the surgical glue is left exactly in the operation region, which limits the dispersion through the nearby tissues. This way, less surgical glue is required, which reduces the probability of:
    surgical glue introduction into the circulatory system through the entry site;
    formation of gross hardened glue lumps under the skin.

The device may have a one-way fluid tight means at a rear end of said short tube, which is arranged in use proximate to said skin plane, said one-way fluid tight means suitable for avoiding the surgical glue from leaking through a corresponding rear end of said narrow space, said one-way fluid tight means comprising, in particular, a sealing ring that is arranged inside said narrow space. The one-way fluid tight means further assists preferential sliding of the surgical glue, once it has been released from the duct, towards the entry site, which in turn assists the interaction with the blood that flows out of the entry site when the introducer sheath is removed.

Advantageously, said sliding coupling means can be actuated while said introducer sheath engages said entry site, such that it is possible to couple said duct with said introducer sheath after arranging said introducer sheath in said entry site.

Preferably, said sliding coupling means that can be actuated while said introducer sheath engages said entry site comprises a short tube that has a longitudinal cut that extends from a front end of said short tube, said front end oriented in use towards said operation region, to a rear end of said short tube, such that by closely aligning and reciprocally compressing said short tube and said introducer sheath, said short tube forms a snap fit with said introducer sheath and a sliding coupling is obtained between said short tube and said introducer sheath.

Advantageously, the introducer sheath and the short tube have a substantially cylindrical shape, and a minimum width portion of the longitudinal cut has a width set between $2/5$ and ⅘ of the short tube diameter. Preferably, the short tube is made of a resilient material such as polyethylene or polypropylene.

Therefore, the short tube can be eventually coupled with the introducer sheath in an easy way, and allows closing the entry site in an effective way. In particular, it is possible to carry out a percutaneous procedure and then the haemostatic procedure at the patient's bed. The snap fit coupling has the advantage of allowing at the same time the duct to be fastened to the introducer sheath and to slide with respect to the introducer sheath, and the outlet mouth of the duct to be in contact with the surface of the introducer sheath, such that the thin wall of the short tube also works as a membrane. In fact, the pressure against the thin short tube exerted by the fluids and by the nearby tissues keeps the short tube in tight contact with the introducer sheath, and only an injection pressure exerted while injecting the glue can exceed this pressure and cause the surgical glue to flow into the channel that has been created by the introducer sheath. Furthermore, the annular short tube assists the outlet flow of the surgical glue along the surface of the introducer sheath, in particular, towards the entry site of the blood vessel.

Advantageously, a block means is provided for blocking a movement of said duct with respect to said introducer sheath. This allows a surgical glue dose to be released at a safe distance from the entry site, thus preventing the hardening material from entering the blood vessel, without any echographic control needed.

Advantageously, the block means is arranged at a distance from the outlet mouth set between 3 mm and 12 mm, preferably between 3 mm and 5 mm. This distance is enough to effectively and safely release the surgical glue, both in the case of a normal patient and in the case of an obese patient. In fact, it has been observed that the femoral artery, where entry sites are normally made, may be at a distance from the skin plane that ranges from about 6 mm to more than 30 mm. The angle of incidence between the puncture direction and the artery can be selected in such a range that the distance between the puncture of the artery and the puncture of the skin plane is always greater than 8 mm. Before the introducer sheath is withdrawn, the surgical glue is prevented from entering the artery by the introducer sheath itself; after the extraction of the introducer sheath, the surgical glue is subject to the pressure that is exerted by the operator on the skin for releasing the glue in the channel. At the same time, the arterial pressure causes the blood to flow out of the entry site, towards the channel. The high reactivity of the surgical glue causes a quick local hardening of the outflowing blood front, which helps to prevent dispersion of the surgical glue through the nearby tissues.

Advantageously, the block means is arranged at a distance from the front end of the duct that is set between 6 mm and 15 mm, preferably between 6 mm and 8 mm. For reasons similar to the above-mentioned ones, this prevents the end of the duct from being placed too close to the entry site, both in the case of an obese patient, and in the case of a normal patient.

Advantageously, the surface of the duct has a line, i.e. a marker, which is traced distally with respect to the block means, for signaling a point at which the movement of the sliding duct along the introducer sheath must be blocked, outside of the skin of a particularly thin patient, in particular the marker is located at a distance set between 3 mm and 5 mm from the outlet mouth.

Thanks to the sliding coupling between the duct and the introducer sheath, the operator, with one hand and without the need to coordinate the movement of more than one limb, can cause the duct to slide and can block it when the block means abuts, and can operate the pressurizing means by one finger, thus causing the release of the surgical glue in the operation region, at a safe distance from the entry site of the artery. In the short time between the release and the hardening of the surgical glue, the surgical glue is prevented from entering the artery by the introducer sheath, which is still inserted in the entry site, as well as by the arterial pressure; the high speed with which the glue locally interacts with the biological means, avoids its dissolution through the nearby tissues.

Preferably, said block means is arranged integral to said duct at a distance from said outlet mouth such that said outlet mouth is at said predetermined distance from said skin plane when said block means abuts against said skin plane.

In alternative, said block means is adapted to abut against a wall of said artery at said entry site, and said outlet mouth is arranged at a predetermined distance from said block means, in order to make an operator aware that said outlet of said duct is ready for releasing said surgical glue proximate to said entry site.

The outlet mouth may be arranged above or laterally with respect to the duct.

Said backflow preventing means may also comprise a check valve that is arranged at said outlet mouth, said valve comprising a fixed part that is fixed with respect to said duct and a movable part that is movable with respect to said fixed part, wherein, when said pressurizing means is operated, said movable part changes its position from:
- a closed position, in which said release of surgical glue is hindered, to
- an open position, in which said injection pressure causes said release of surgical glue at said operation region.

In alternative, said liquid contact preventing means comprises:
- a liquid retaining means for retaining a barrier liquid inside said duct;
- a liquid outflow means that can be operated by said operator for causing an outflow of said barrier liquid through said duct, such that:
- said barrier liquid interposes between said surgical glue and said outlet mouth, and such that
- by operating said liquid outflow means and said pressurizing means, said barrier liquid flows out of said outlet mouth before said surgical glue, such that said surgical glue is substantially undiluted when it is released at said operation region.

The duct may be selected from the group comprised of:
- a conventional needle, to be used for example in the haemostasis of arterial entry sites, pseudoaneurysms or small aneurysms;
- a catheter, to be used for reaching remote operation regions through an endovascular path, said remote operation regions located far from an entry site.

Finally, during the injection into a blood vessel in which the blood flows, the barrier liquid, which is released first, is washed away by the blood flow; therefore, when the surgical glue is released, the high reactivity of the surgical glue with the blood is substantially unchanged, which ensures that the interaction is carried out to completion locally.

Advantageously, the device comprises a container for said barrier liquid, said container selected from the group comprised of:
- a portion of said duct;
- a receptacle that in use is hydraulically connected to said duct. This feature assists safe operation, since it reduces the possibility of mistakes that might otherwise be made when selecting a barrier liquid at the moment of the use; moreover, the feature allows a more practical operation.

The receptacle may have an inlet port and an outlet port, preferably with respective connecting means to connect the receptacle with the container of the device and with the duct. Advantageously, the receptacle is available in sizes responsive to the barrier liquid need, which is in turn responsive to the distance of the operation region from the device, in particular endovascular interventions require much more barrier liquid than what is needed to treat an arterial entry sites.

Preferably, said container contains said barrier liquid, in particular, a barrier liquid selected from the group comprised of:
 a saline solution;
 a glucose solution;
 distilled water;
 a liquid contrast agent.

The use of a liquid contrast agent as a barrier liquid allows using a radiographic means for displaying the point that has been selected for releasing the surgical glue, since surgical glues cannot be seen by a radiographic means. On the other hand, not all the vascular zones can be shown by an echographic means, due to the presence of air or of bones, which causes unfeasibility of many interventions under echographic control, for example thoracic, abdominal or cerebral interventions. Many surgical glues, in particular cyanoacrylate glues, can in any case be detected by an echographic means and can therefore be used under echographic control, if possible, and a saline solution may then be used as the barrier liquid.

Advantageously, said liquid outflow means can be operated independently from said pressurizing means. This way, the operator can arrange the duct up to reach the operation region by the outlet mouth, without suffering the effects of blood pressure, or, in any case, the effects of the resistance offered by the tissues while they are crossed by the duct: in fact, the liquid that is retained inside the duct behaves as an integral part of the duct and the rest of the device. In particular, a blood backflow or suction may not occur while the duct is being positioned.

Preferably, the device comprises a protection means for avoiding accidental operation of said pressurizing means before said outflow of said barrier liquid.

Preferably, the device comprises a sealing member for isolating said barrier liquid in said container, wherein said sealing member can be removed or broken by an action selected from the group comprised of:
 operating said liquid outflow means;
 operating said pressurizing means;
 connecting said duct with said container of said barrier liquid;
 a combination of such operations.

This way, the surgical glue is prevented from mixing with the barrier liquid before its application, which would decrease its efficiency. The duct that contains the barrier liquid can be for example a needle or a catheter whose inlet port has a seal that can be broken by joining the catheter with the container, and whose outlet mouth has a manually removable seal.

Advantageously, said liquid contact preventing means comprises, furthermore, a locking means that is selected from the group comprised of:
 a locking means of said liquid outflow means,
 a locking means of said pressurizing means;
such that a backward movement of said liquid outflow means and of said pressurizing means, respectively, is prevented;
 a combination of said locking means.

This feature assists the operator while positioning the duct that retains the barrier liquid, since the operator would otherwise be obliged to apply a force for contrasting the backpressure exerted by the blood and the resistance due to the friction, but without causing a release of the surgical glue until the positioning is completed. In this case, a protection means is preferably provided for avoiding accidental operation of the liquid outflow means.

The device can also comprise a further receptacle that contains said surgical glue, wherein, in particular, said surgical glue comprises a cyanoacrylate, more In particular, a cyanoacrylate that is selected from the group comprised of: N-butyl-2-cianoacrylate and 2-octyl-2-cianoacrylate. These compounds give origin to highly biocompatible and particularly flexible polymers, which have been successfully used to reconstruct damaged tissues. The device according to the invention allows to widen the use of the above-mentioned surgical glues to percutaneous endovascular interventions, such as embolizations of blood vessels, treatments of arteriovenous malformations or of small aneurysmatic diseases, for example of small cerebral aneurysms, arterial dissections, and the like; furthermore, it allows their use in the haemostasis of arterial entry sites. In particular, in this case, the cyanoacrilates quickly react both with the blood and with other biological liquids that are present in the operation region, hardening the periadventitial tissues and the fat surrounding them, substantially sticking such materials on the wall of the artery, and creating at the entry site an acrylic polymer matrix, which incorporates the above-mentioned biological materials, and which works as a plug that is firmly adherent to the wall of the artery. The quick formation of the matrix stops the blood outflow and allows the completion, in an independent way, of the natural repair processes of the arterial wall, which are no longer disturbed by the blood outflow through the entry site. Such substances as the cyanoacrilates provide therefore an occlusion system that is new with respect to well known occlusions systems, which, on the contrary, form plugs or clots that are involved in the normal coagulation mechanisms, and which, for this reason, may cause the above mentioned complications.

In particular, the device comprises a double syringe which, in turn, comprises:
 an internal syringe that comprises a first piston that one-way fluid tightly slides inside a first cylinder, said first cylinder having a base with a portion that comprises said frangible seal and is opposite to said first piston;
 an external syringe that comprises a second cylinder and said internal syringe that one-way fluid tightly slides in said second cylinder, said second cylinder having a base that is opposite to said internal syringe with a tail portion, said tail portion having an outlet hole, and a tip member that is oriented towards the inside of said second cylinder and is adapted to break said frangible seal when said base of said first cylinder approaches said base of said second cylinder, wherein said internal syringe provides said further receptacle for said surgical glue and said first piston provides said pressurizing means,
wherein said external syringe provides said receptacle for said barrier liquid and said liquid outflow means which can be operated independently from said pressurizing means,
wherein a means is provided for mechanically locking said first syringe at a final position within said second cylinder and said first piston at a predetermined starting position within said first cylinder, wherein preferably a cap is provided which is releasably connected with said first cylinder in order to provide said protection means for avoiding accidental operation of said pressurizing means.

According to a further aspect of the invention, the above-mentioned objects are achieved by a device for closing a percutaneous entry site of a blood vessel, in particular, an entry site of an artery or of a vascular prosthesis, said entry site engaged by an elongated introducer sheath, the device comprising a duct and a sliding coupling means that is adapted to couple said duct with said introducer sheath, said duct having an outlet mouth, said duct adapted to convey a dose of a surgical glue and to release said dose through said outlet mouth in an operation region at a predetermined distance from the skin plane close to said operation region, said dose of a surgical glue adapted to make an occlusion that prevents a bleeding from said entry site when said introducer sheath is withdrawn from said entry site, the main feature of the device being that the device comprises a block means for blocking a movement of said duct with respect to said introducer sheath, wherein said block means is arranged integral to said duct at a distance from said outlet mouth such that said outlet mouth is at said predetermined distance from said skin plane when said block means abuts against said skin plane.

The above-mentioned objects are achieved also by a method for blocking a flow of blood of an artery to cause a release of a surgical glue in an operation region in a patient's body, said method providing the steps of:
- prearranging a duct that has an inlet port and an outlet mouth for said surgical glue;
- inserting said duct through an opening on a skin plane of said patient;
- advancing through a biological medium of the patient's body until said operation region is reached, in such a way that, once reached said operation region, said outlet mouth is in said operation region and said inlet port remains outside of said opening in said skin plane;
- hydraulically connecting said inlet port with a source of said surgical glue and with a pressurizing means that can be operated by an operator for applying an injection pressure on said surgical glue;
- operating said pressurizing means causing an outflow of said surgical glue through said duct and said release of surgical glue at said operation region through said outlet mouth;

the main feature of said method is that a step is provided of prearranging a liquid contact preventing means that is associated to said duct, said liquid contact preventing means adapted to impede in said duct a contact of said surgical glue with said biological medium before said outflow, in particular, a contact of said surgical glue with blood of said patient.

The operative steps of the method work to carrying out the device according to the invention, as above described.

In particular, before said step of prearranging a liquid contact preventing means, a step is provided of
- coupling said duct with an elongated introducer sheath that is arranged between said opening on said skin plane and a vascular entry site.

Preferably, said step of advancing is carried out by causing a translation on said introducer sheath of said duct slidingly coupled on said introducer sheath.

Advantageously, said outflow is carried out towards said introducer sheath such that said surgical glue is released and flows along said introducer sheath. In particular, said surgical glue is released in an annular narrow space that is defined between said short tube and said introducer sheath such that said surgical glue reaches said operation region through said annular narrow space.

Advantageously, said method provides a step of prearranging a block means integral to said duct, said block means adapted to engage with said skin plane during said step of advancing, said step of advancing stopped when said block means abuts against said skin plane.

In alternative, said method provides a step of
- prearranging a liquid retaining means for retaining a barrier liquid in said duct;
- selecting a barrier liquid;
- introducing said barrier liquid into said duct;
- prearranging a liquid outflow means for causing an outflow of said barrier liquid through said duct;
- operating said liquid outflow means, such that said barrier liquid interposes between said surgical glue and said outlet mouth, and such that by operating said liquid outflow means and said pressurizing means, from said outlet mouth firstly a release of said barrier liquid occurs and then said release of surgical glue occurs, such that said surgical glue is substantially undiluted when it is released at said operation region.

BRIEF DESCRIPTION OF THE DRAWINGS

The invention will now be made clearer with the following description of an embodiment thereof, exemplifying but not limitative, with reference to the attached drawings wherein:

FIGS. 4 and 5 show a perspective view and a cross sectional view of a device according to another exemplary embodiment of the invention, in which the duct comprises a needle;

FIG. 21 shows a device similar to the device of FIG. 6, comprising, furthermore, a blocking means for preventing the duct from moving with respect to an introducer sheath;

FIGS. 22 and 23 are similar devices to the device of FIG. 7, wherein a block means is provided according to two different exemplary embodiments;

FIG. 24 diagrammatically shows a device similar to the devices of FIGS. 21-23, which is coupled with an introducer sheath, which in turn engages an arterial entry site;

DESCRIPTION OF PREFERRED EXEMPLARY EMBODIMENTS

Figure 1:
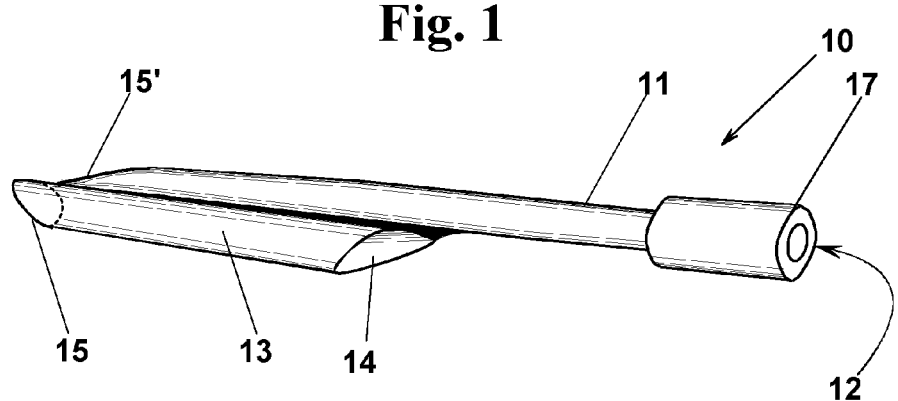
FIGS. 1 and 2 show a perspective view and a cross sectional view of a device according to an exemplary embodiment of the invention, wherein a coupling means is provided with a catheter introducer sheath that has a short tube that is co-axial to the introducer sheath.
Figure 2:
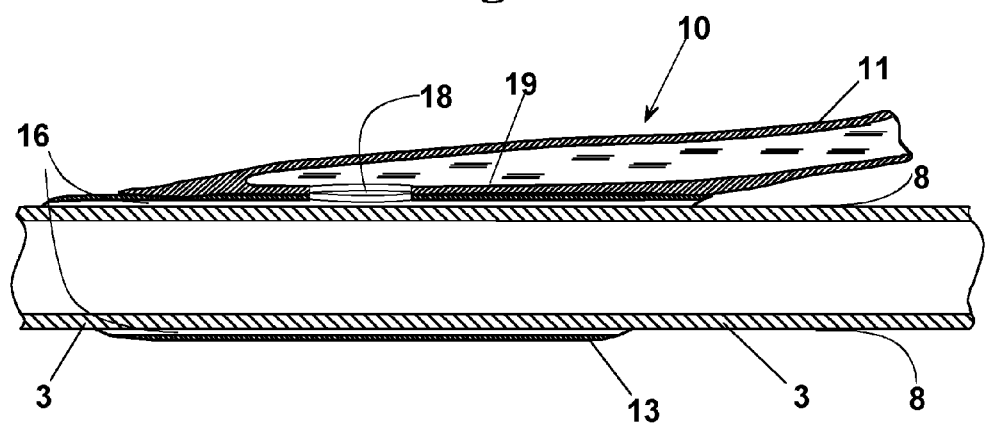
Figure 3:
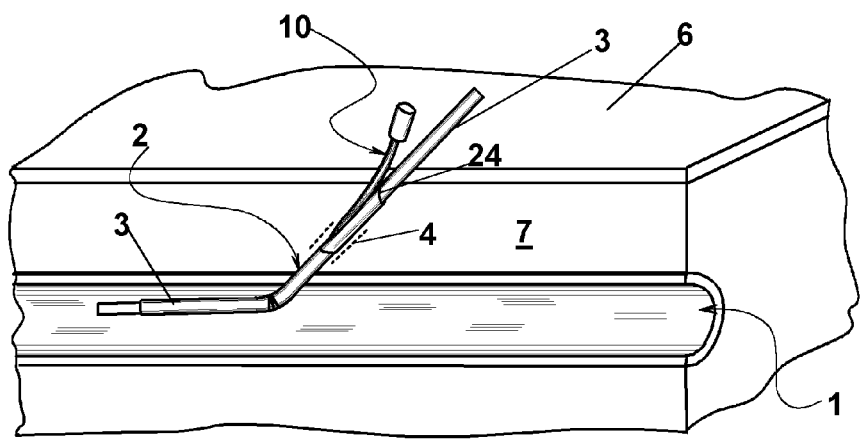
FIG. 3 shows the device of FIGS. 1 and 2 that is coupled with an introducer sheath, which engages a vascular entry site.

With reference to FIGS. 1, 2 and 3, a device 10 is described according to a first exemplary embodiment of the invention, for closing an entry site 2 in a blood vessel 1, or in a vascular prosthesis 1 (FIG. 3). A substantially cylindrical catheter introducer sheath 3, engages entry site 2. Device 10 (FIG. 1) comprises a duct 11 that has at one end an inlet port 12 that is associated with a luer-lock connection 17, or other connection suitable for connecting a source, not shown, of a surgical glue 9, for example a receptacle of a syringe. In the description, reference is made to a surgical glue, still remaining that the device can be advantageously used with any quick setting haemostatic liquid. At the opposite end, instead, an outlet mouth 18 (FIG. 2) is provided for surgical glue 9. For carrying out the haemostasis, outlet mouth 18 must be located at an operation region 4 (FIG. 3). A short tube 13, with a substantially cylindrical or slightly conical shape, and shorter than duct 11, is arranged integral to duct 11 along a generatrix of it, at the end of duct 11 opposite to the end of inlet port 12, short tube 13 is open at its two ends 14 and 15, which are respectively the rear end and the front end, and is coupled, in use, with introducer sheath 3 (FIG. 3), providing in this way a coupling means of duct 11 with introducer sheath 3.

Outlet mouth 18 (FIG. 2) is arranged between duct 11 and the outer surface 8 of introducer sheath 3, and the coupling between short tube 13 and introducer sheath 3 is made in such a way that outlet mouth 18 is kept into tight contact against outer surface 8 of introducer sheath 3, and that outlet mouth 18 detaches from outer surface 8 only when an operator, using a means provided by the device, applies an injection pressure to surgical glue 9, causing the release of surgical glue 9 from duct 11 into operation region 4 (FIG.3) through an annular narrow space 16 (FIG. 2) that is formed between short tube 13 and a portion of outer surface 8 of introducer sheath 3. This way, short tube 13 provides a backflow preventing means, which serves to prevent any contact of surgical glue 9 with a biological material 7 (FIG. 3) that device 10 crosses while approaching outlet mouth 18 to operation region 4.

The coupling of duct 11 with introducer sheath 3 can be a slidable or a fixed one, according to whether short tube 13 can slide or not along the outer surface of introducer sheath 3. In the latter case, device 10 is positioned with outlet mouth 18 in the operative region since the beginning of the endovascular procedure, together with introducer sheath 3, whereas in the former case it is preferably slided towards the operation region 4 at the end of the procedure, i.e. when the introducer sheath must be withdrawn, in order to prevent bleeding from entry site 2. To assist device 10 sliding in the patient's body, front end 15 (FIG. 1) of the short tube, and front end 15' of the duct 11 have a tapered shape. Short tube 13 and duct 11 preferably form one piece obtained by moulding.

FIGS. 4 and 5 show a perspective view and a partial cross sectional view, respectively, of a device 20 according to another exemplary embodiment of the invention, in which duct 11, which is integral to short tube 13 (FIGS. 1 and 2), is replaced by a duct 21, in particular, by a duct that is made by a syringe needle that is tightly inserted in a connecting tail portion 22 of short tube 13, such that outlet mouth 18 is located at a passage 29 between the inside of short tube 13 and connecting tail portion 22. Connecting tail portion 22, and therefore duct 21, forms an angle 26 with short tube 13, which is preferably set between 10° and 20°. Duct 21, in particular if it comprises a syringe needle, or a metal capillary tube, is flexible, and can therefore be permanently bent as desired by the operator, according to specific needs. Also in this exemplary embodiment, short tube 13 provides both a backflow preventing means and a coupling means between the duct and the introducer sheath.

Figure 6:
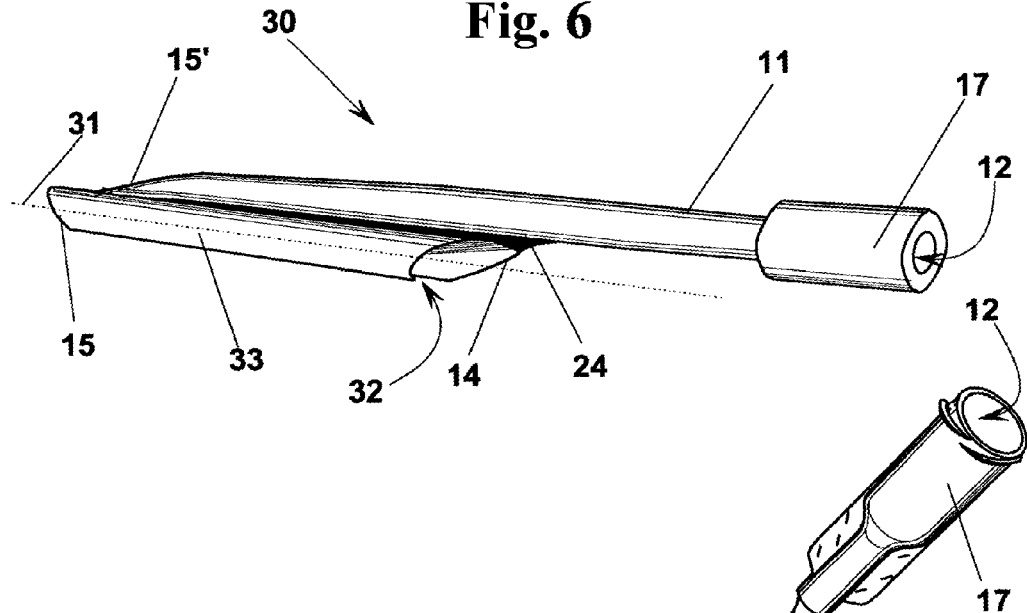
FIGS. 6 and 7 show a perspective view of a device similar to the devices of FIGS. 2 and 4, in which the short tube is slidingly coupled and to snap fitted with an introducer sheath at the end of an endovascular procedure.
Figure 7:
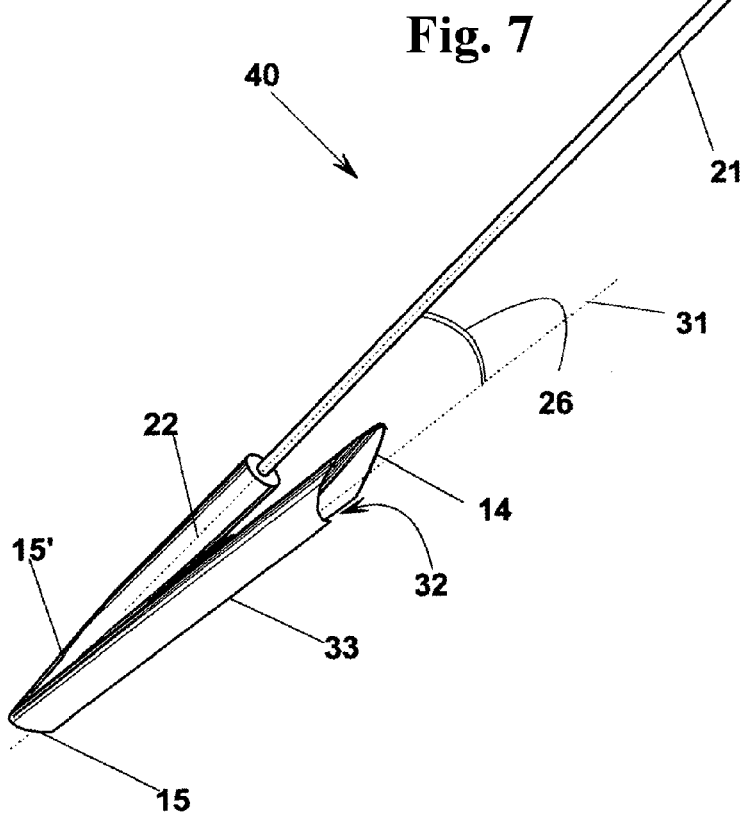
Figure 8:
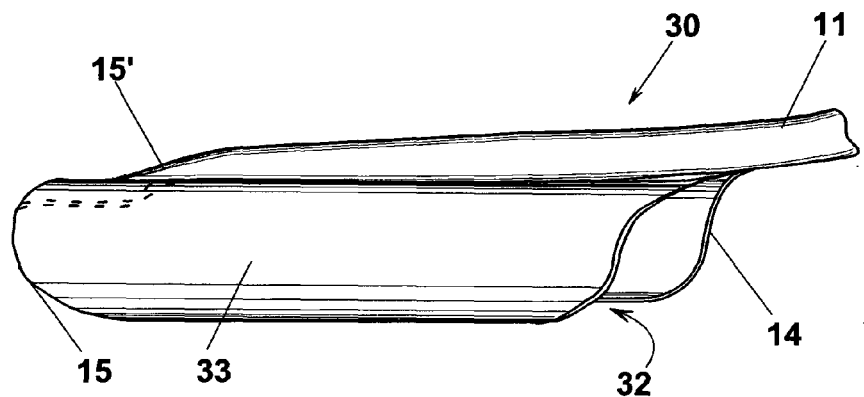
FIG. 8 is a perspective view of a particular of the device of FIG. 7.
Figure 9:
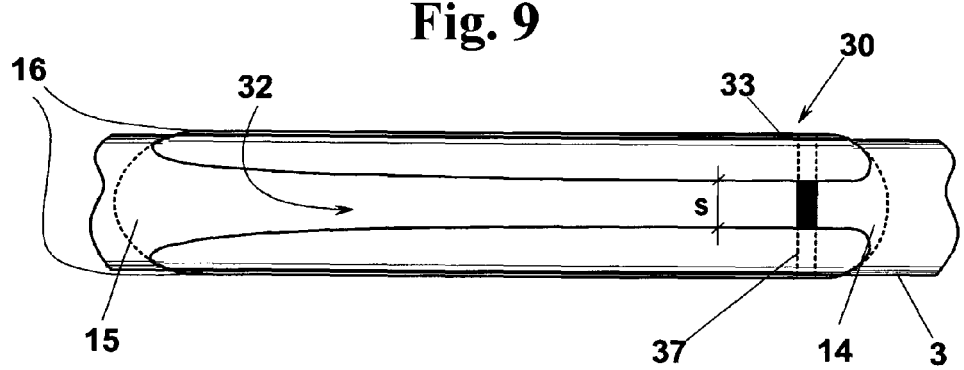
FIG. 9 shows the device of FIG. 8 mounted on an introducer sheath, and have a rear one-way fluid tight means.

FIGS. 6 and 7 show a perspective view of two devices 30 and 40 that differs from devices 10 and 20, respectively, in that the short tube 33 has a longitudinal cut 32 from the end 14 to the opposite end 15, along the generatrix of short tube 33 that is located opposite of duct 11 with respect to the axis 31 of short tube 33, which is more clearly shown in the detail view of FIG. 8. As shown in FIG. 9, longitudinal cut 32 has preferably an increasing width, proceeding from rear end 14 to front end 15, with a minimum width s of about ⅓ of the diameter of introducer sheath 3, which forms a snap fit with short tube 33 about introducer sheath 3, in such a way that a sliding connection is obtained. This way, device 30 can be applied at the end of the diagnostic or interventistic procedure for which the entry site to blood vessel 1 has been made.

Independently from whether longitudinal cut 32 is present or not, sealing means may be provided for avoiding that surgical glue 9 flows out of annular narrow space 16 (FIG. 2) through rear end 14 of short tube 33, which is oriented towards the skin 6 (FIG. 3). In this exemplary embodiment, the one-way fluid tight means comprises a sealing ring 37 (FIG. 9). Still to assist a surgical glue flow through front end 15 of short tube 33 towards entry site 2, the cross section of the one piece comprising the duct and the short tube increases from the front end to the rear end, a part of the cross sectional increase due to the tapering surface at front end 15' of duct 11 and to the local thickening 24 of the wall of short tube 13 or 33 (FIGS. 5 and 6).

Further embodiments of the backflow preventing means, in alternative to the embodiment of devices 10, 20, 30, 40, are shown through FIGS. 11 to 14. These figures reproduce partial views of devices 50 and 60, in which a backflow preventing means is provided by check valves 55 and 65 at outlet mouth 18 of duct 11; check valves 55 and 65 comprise respective fixed parts 53 and 63 and movable parts 54 and 64. Movable parts 54 and 64 are kept in the closed position of FIGS. 11 and 13 by the pressure P1 that the tissues of the operation region 4 (FIG. 4) exert outside the walls of duct 11; at the moment of the injection of the surgical glue contained in duct 11, an injection pressure $P_2$ exerted on the liquid by an operator through a means of the device, not shown, overcomes the pressure $P_1$ and brings movable parts 54 and 64 in the open positions of FIGS. 12 and 14, and surgical glue 9 is released.

Further embodiments of the coupling means, in particular, of the sliding coupling means, between duct 11 and introducer sheath 3, in alternative to the embodiments of devices 10, 20, 30, 40, are shown through FIGS. 15 to 20. These figures reproduce partial views of devices 70 and 80 in which a duct 71 or 81 has a slide portion that slidingly engages with respective driving portions 77 and 87 of introducer sheath 3. In particular, in device 70 duct 71 itself can slide as a sliding portion within a driving portion provided by a longitudinal groove 77 of introducer sheath 3. Longitudinal groove 77 has a shape suitable for retaining duct 11, for example by means of an undercut portion, not shown. In device 80, a duct 81 has a slide portion 82 that can slide along a longitudinal groove 87 of introducer sheath 3; the slide portion of duct 41 is then connected to a rear tubular portion by a connecting portion 84.

Figure 17:
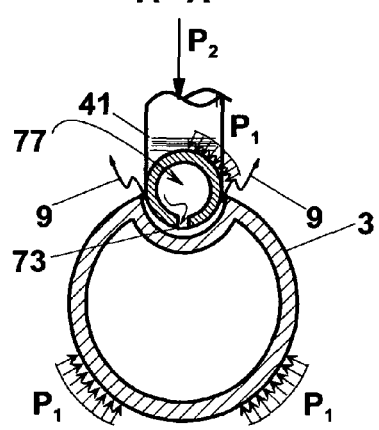
Figure 18:
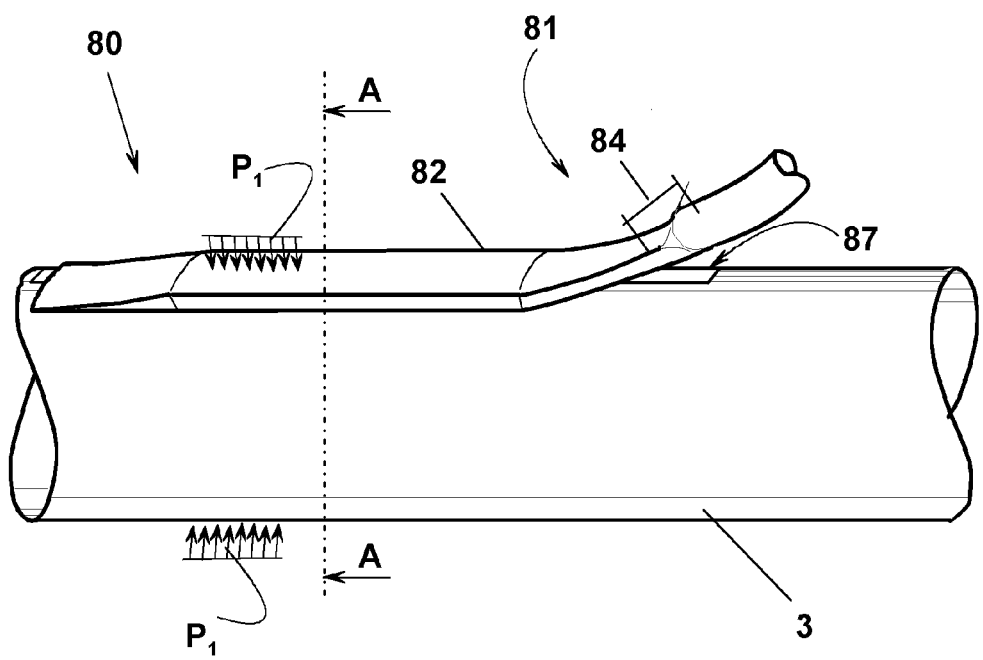
FIGS. 18, 19 and 20 are Figs. similar to FIGS. 15-17, referring to an exemplary embodiment of a backflow preventing means and to a sliding coupling means between the duct and an introducer sheath.
Figure 19:
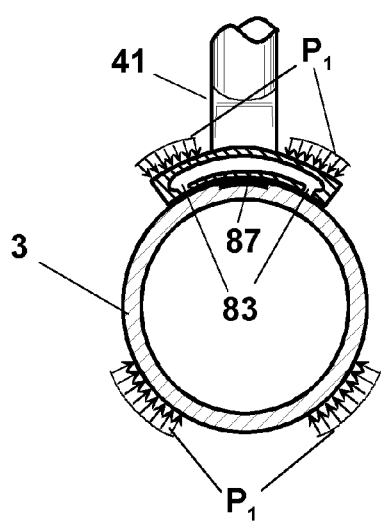
Figure 20:
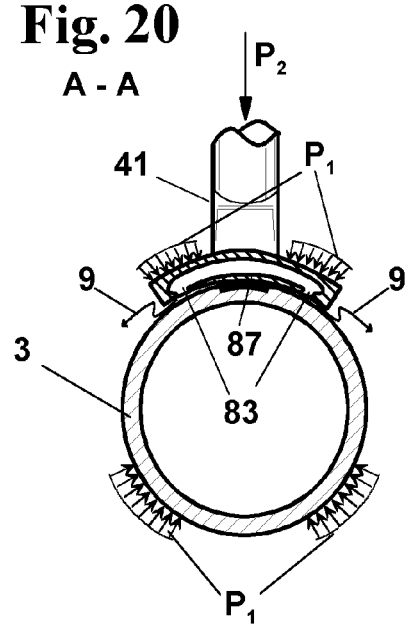

In devices 70 and 80 a backflow preventing means is provided by the connection between duct 71 or 81 and introducer sheath 3, which is made in to such a way that an outlet mouth 73 or 83 is positioned between duct 11 and introducer sheath 3, and that the outlet mouth is kept into tight contact against introducer sheath 3 by pressure P1 exerted by the tissues of operation region 4 (FIGS. 16 and 19); at the moment of the injection of surgical glue 9, an injection pressure $P_2$ exerted on the liquid by an operator through a means of the device, not shown, overcomes the pressure $P_1$ and locally detaches duct 11 from introducer sheath 3, in such a way that outlet mouths 73 or 83 are opened, and surgical glue 9 is released (FIGS. 17 and 20).

Also in the devices of FIGS. 11-20, above described, the connection between duct 11 and introducer sheath 3 can be a fixed connection or a sliding connection along introducer sheath 3.

Figure 10:
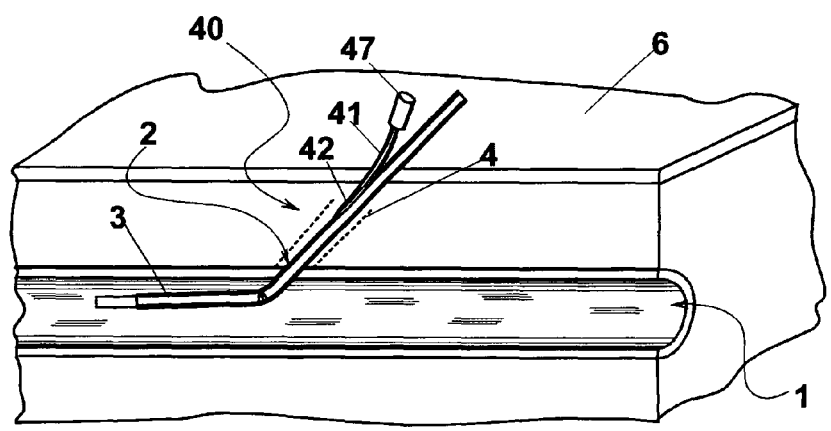
FIG. 10 shows a generic device 3 coupled with an introducer sheath, which in turn engages an arterial entry site.
Figure 11:
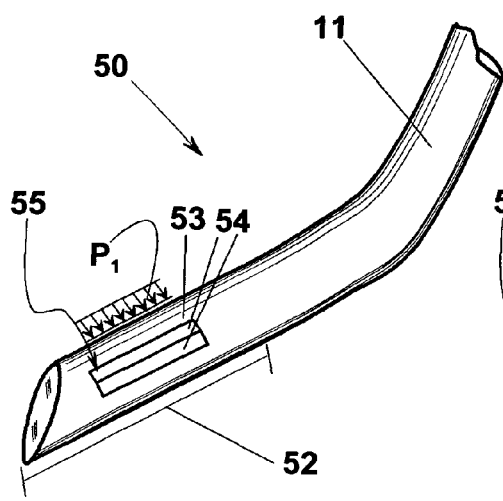
FIGS. 11 and 12 are a views of a detail of the duct of a device according to the invention, with an exemplary embodiment of a backflow preventing means, that has a check valve which is shown, respectively, in a closed position and in an open position.
Figure 12:
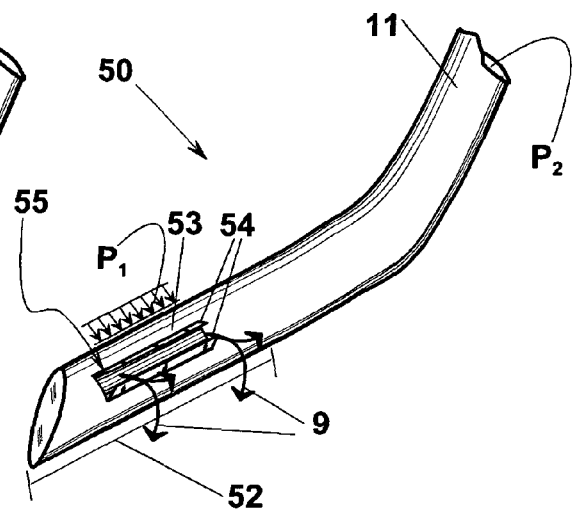
Figure 13:
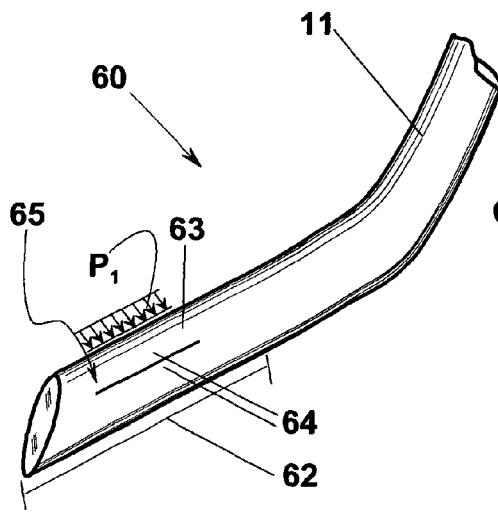
FIGS. 13 and 14 are Figs. similar to 12 and to 13, referring to an exemplary embodiment of the check valve.
Figure 14:
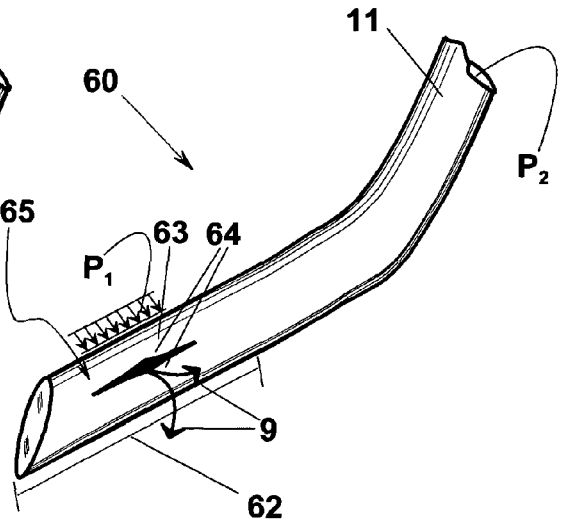
Figure 15:
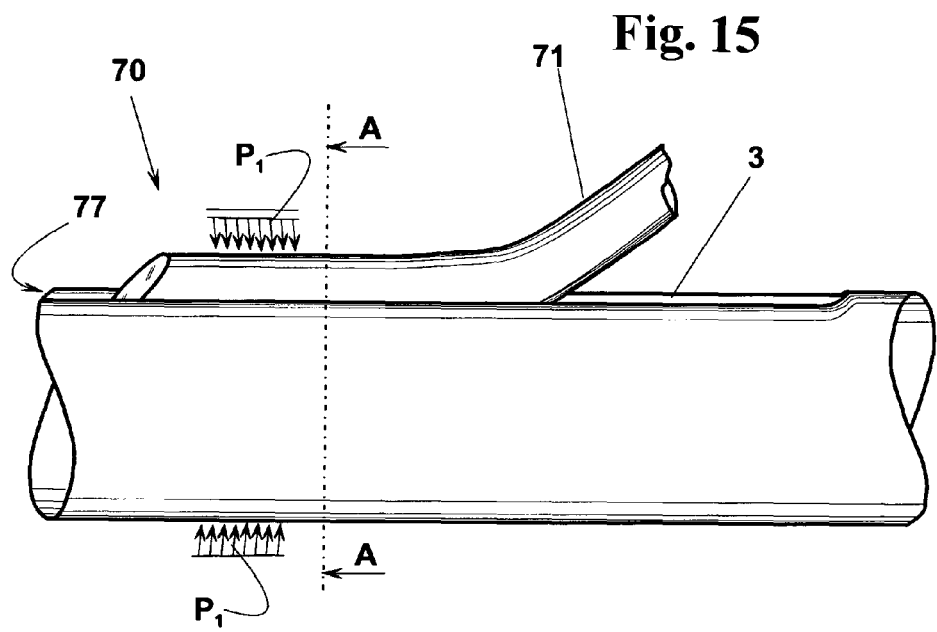
FIGS. 15, 16 and 17 show a detail of a device according to the invention, with an exemplary embodiment of a sliding coupling means between the duct and an introducer sheath, and of the backflow preventing means of the duct.
Figure 16:
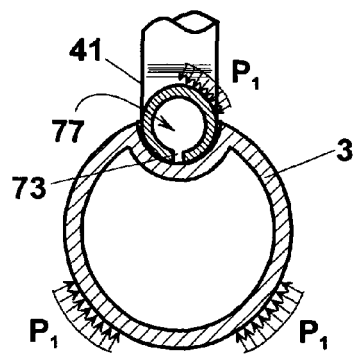

FIG. 21 shows a device 90, according to an exemplary embodiment of the invention, wherein a block means is provided against skin plane 6, which comprise an abutment 94 that is arranged at a distance b from the outlet mouth, the distance b set between 3 and 12 mm, whereas the distance d of abutment 94 from front end 15 is set between 6 mm and 15 mm, such that, when abutment 94 hits skin plane 6, the outlet mouth safely releases surgical glue 9, without any risks of inlet into the blood vessel through entry site 2 (FIG. 10). This distance is the same both in the case of a normal patient, and in the case of an obese patient. In fact, the angle 89 that is defined between the direction of introducer sheath 3 and the local direction of a blood vessel 1 (FIG. 24) may be selected in a range of values that allows compensating the difference of thickness h of the tissues between skin plane 6 and blood vessel 1, leaving unchanged the thickness 8 that must be crossed for positioning the point of release of the surgical glue at the operation region 4. In the case of particularly thin patients, a marker 96 can be traced on the surface of duct 11 at a distance set between 3 mm and 8 mm from the outlet mouth, for signaling to the operator the point at which the sliding movement of duct 11 along introducer sheath 3 must be blocked.

FIGS. 22 and 23 are partial views of devices in which duct 21 is made as it is in devices 20 and 30 of FIGS. 4 and 6, and in which the block means has an exemplary embodiment that is an alternative to the one that is shown in FIG. 21. In FIG. 23, the block means 97 is far smaller than in FIG. 21, whereas the block means 98 of FIG. 22 are made only about connecting tail portion 12.

Figure 25:
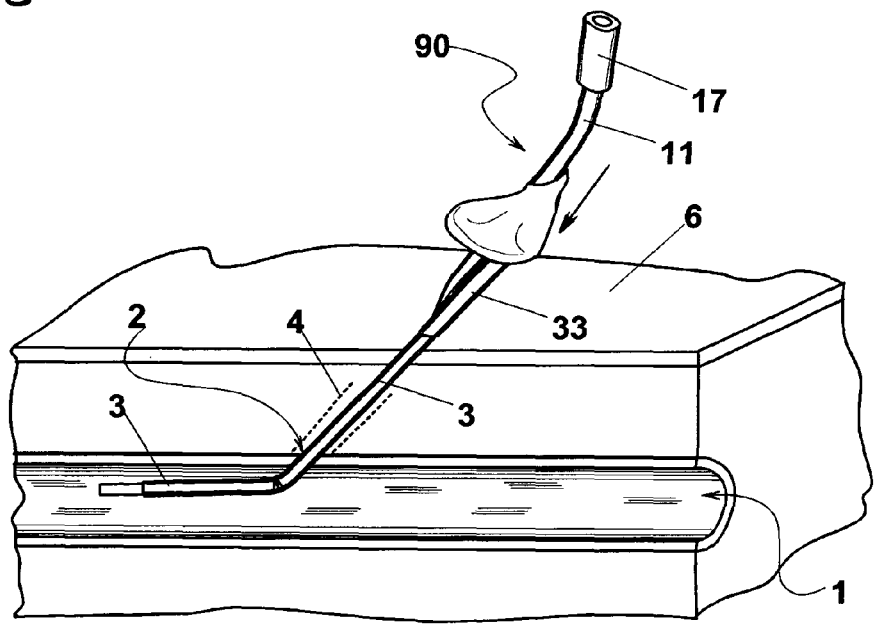
FIGS. 25 to 31 show diagrammatically how to use of the device shown in FIGS. 22-24.
Figure 26:
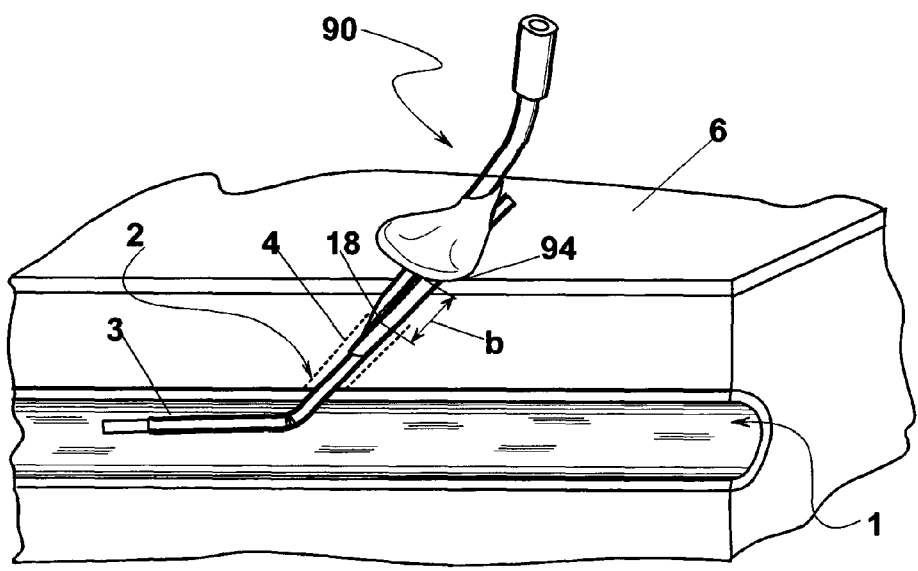
Figure 27:
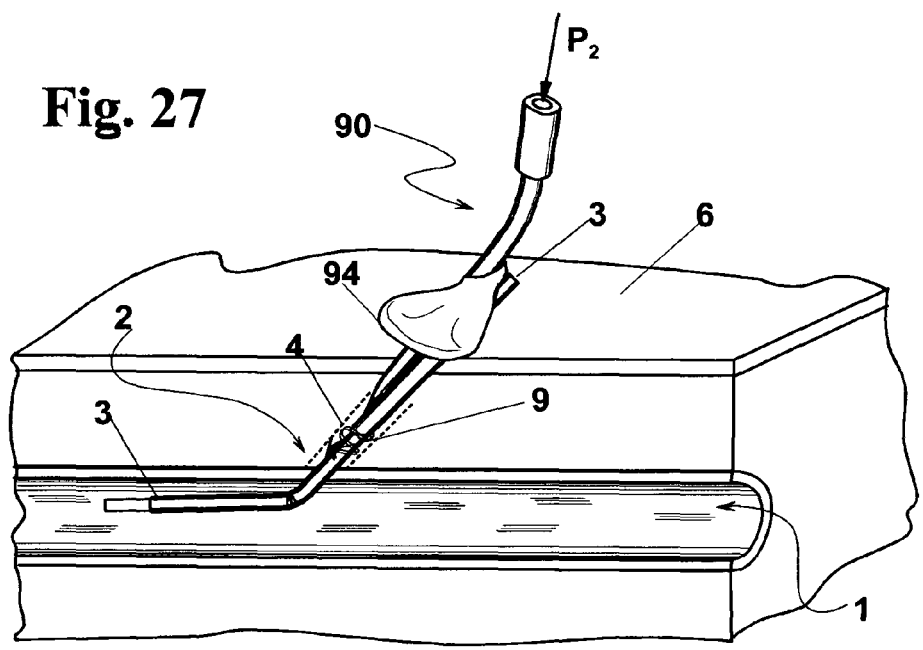
Figure 28:
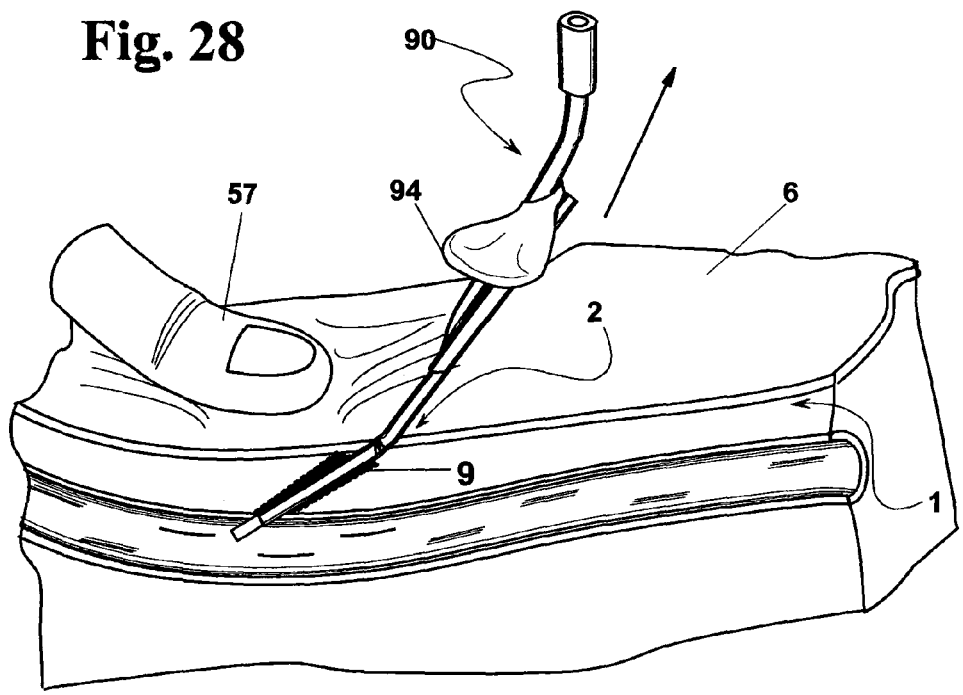
Figure 29:
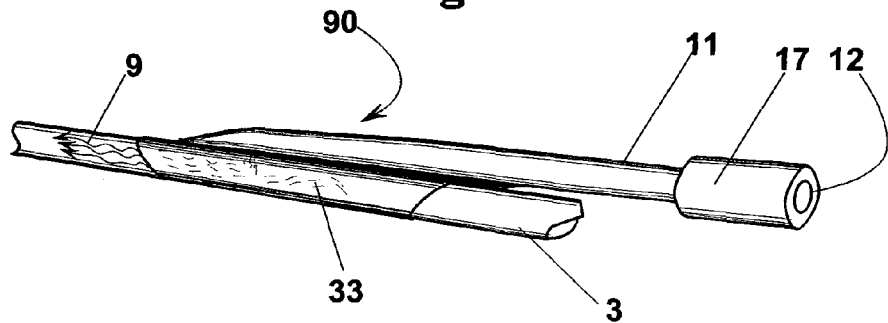
Figure 30:
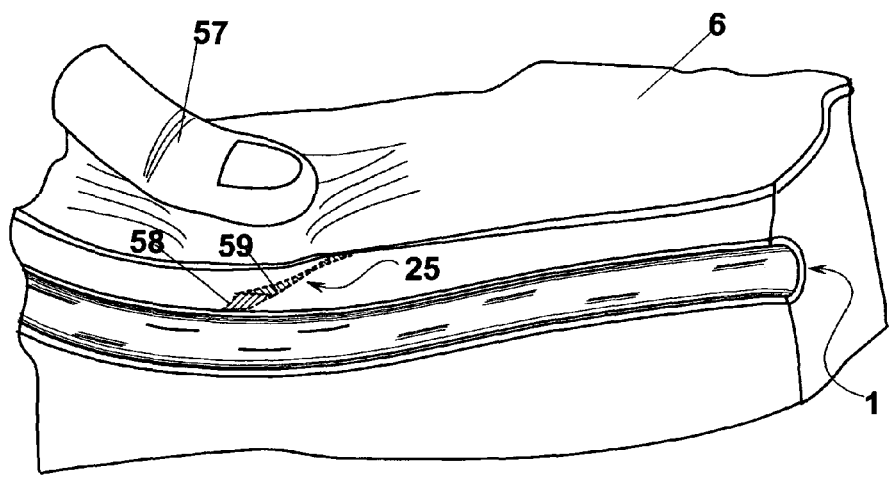
Figure 31:
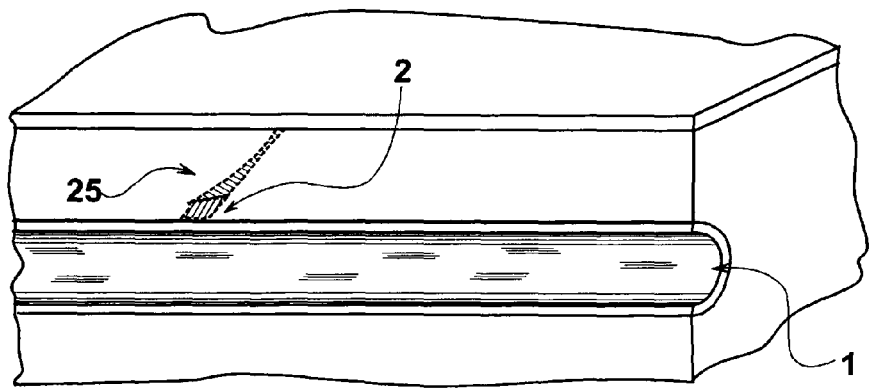

FIGS. 25 to 31 describe how to use a device, according to the invention, for closing a vascular entry site 2, which is engaged by an introducer sheath 3, in particular a device 90 that has a block means. A dose of a surgical glue 9 is prepared in a conventional container, not shown, for example a syringe, which is connected with duct 11 of device 90 by a fitting 17, for example a luer-lock fitting, such that duct 11 can receive the surgical glue. Device 90 is arranged proximate to introducer sheath 3 with short tube 13 closely aligned to introducer sheath 3 against which it is pressed, in such a way that a sliding coupling can be established (FIG. 25). This coupling is tight, in order to prevent the blood and other organic material that is present between the skin 6 and entry site 2 from penetrating into duct 11 when device 90 slides along introducer sheath 3 towards entry site 2 (FIG. 26), and until the surgical glue receives an injection pressure. As shown in FIG. 26, short tube 13 is slided along the introducer sheath towards skin plane 6 and then below it, until abutment 94 hits skin plane 6. Outlet mouth 18, which is made at the inner surface of the short tube (FIG. 2) is located then at a distance b from skin plane 6, which is set between 3 and 12 mm (FIG. 26). Through a pressurizing means for applying an injection pressure on the surgical glue 9, for example through the walls of the container, the operator produces an injection pressure on the surgical glue pushing it through duct 11 and outlet mouth 18 (FIGS. 2 and 27) against the surface of introducer sheath 3. Surgical glue 9 travels between short tube 13 and introducer sheath 3, evenly distributing itself along the surface of the latter, as shown in FIG. 29, and is partially released at operation region 4, where it spreads preferentially in a zone that is immediately around introducer sheath 3, where the cohesion of the tissues is weakened by the presence of introducer sheath 3, without casually dispersing through the nearby tissues. This allows limiting the amount of surgical glue that is needed for closing entry site 2, with economic benefits, less formation of hardened liquid lumps under the skin and higher safety against the inlet of surgical glue into blood vessel 1. Then, the operator compresses with a finger 57 skin 6 near the percutaneous entry site (FIG. 28) and, while maintaining this compression, withdraws device 90 through skin 6. The compression assists first disengaging surgical glue 9 from the surface of introducer sheath 3 and its release in a channel 25 that is left behind by the extraction of device 90; a few further minutes of compression (FIG. 30) are necessary to assist a rear portion 59 of channel 25 to close owing to the surgical glue that interacts with the tissues that are crossed by the introducer sheath, in particular fat, fascia and lymph, incorporate such material into a matrix that sticks together the walls of the channel, sealing it. In a front portion 58 of channel 25, proximate to entry site 2, surgical glue 9 interacts with the blood, with the periadventitial tissues and the wall of blood vessel 1 creating a true plug that is firmly adherent to the wall of blood vessel 1. Below this plug the natural reparative processes of the wall of blood vessel 1 will be carried out to completion in the following days until a full restitutio ad integrum is achieved. The cyanoacrilate-based surgical glues, in particular, react much more quickly with blood than with the other biological material, which immediately stops the bleeding.

Figure 32:
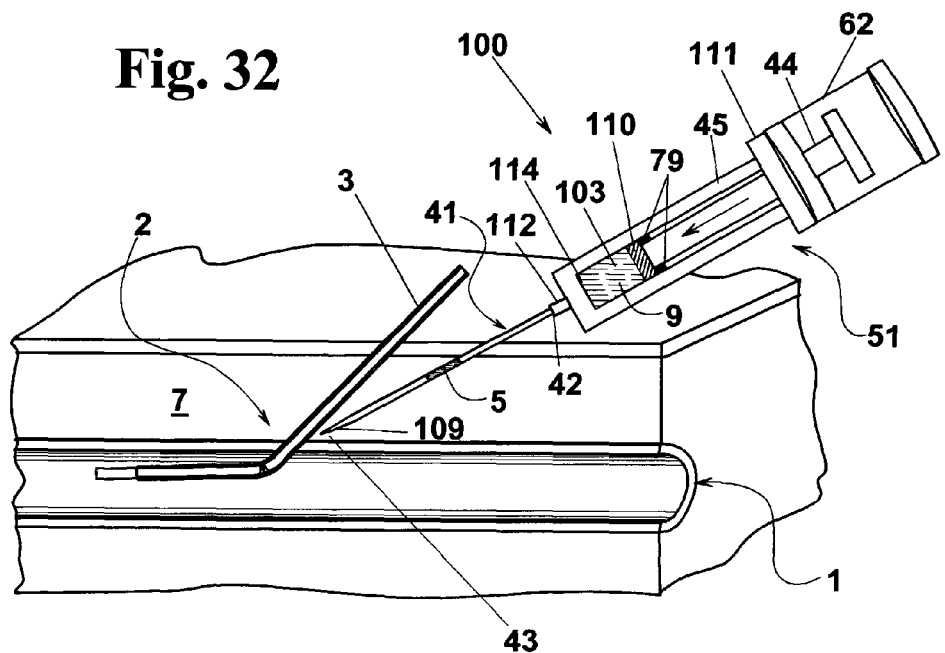
FIG. 32 shows a device according to an exemplary embodiment of the invention, wherein a duct is provided which has a means for retaining an amount of barrier liquid that can be released before the surgical glue, in the case of the figure, for clogging a vascular entry site.
Figure 33:
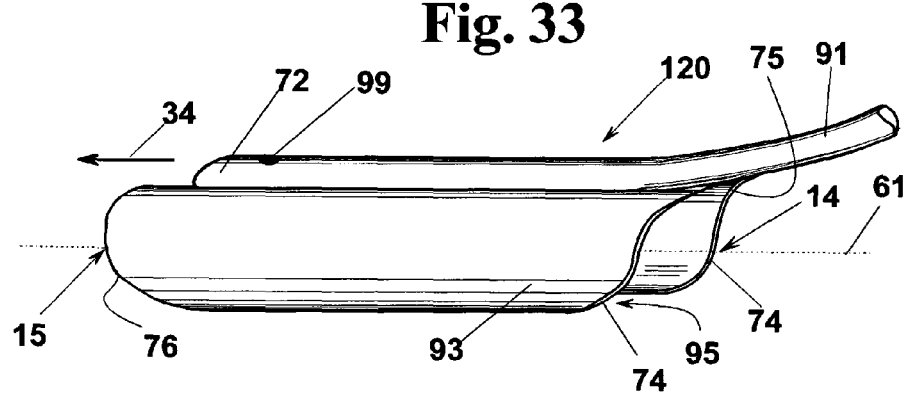
FIGS. 33 and 34 are two perspective views of a detail of a device according to the invention, that is adapted to release a barrier liquid before the surgical glue, for clogging a vascular entry site.
Figure 34:
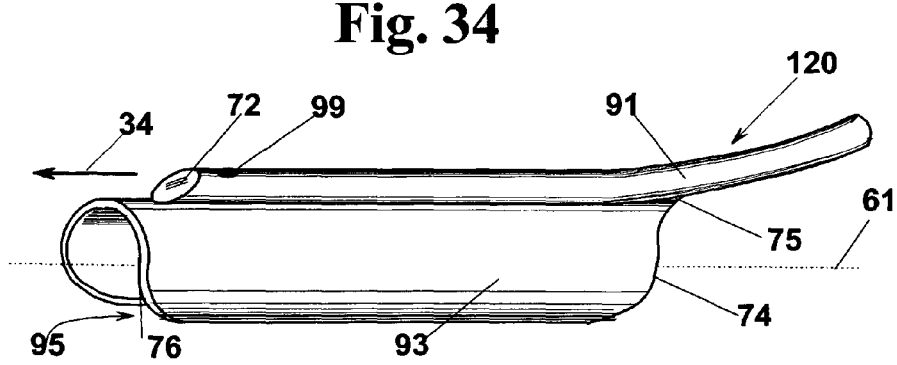
Figure 35:
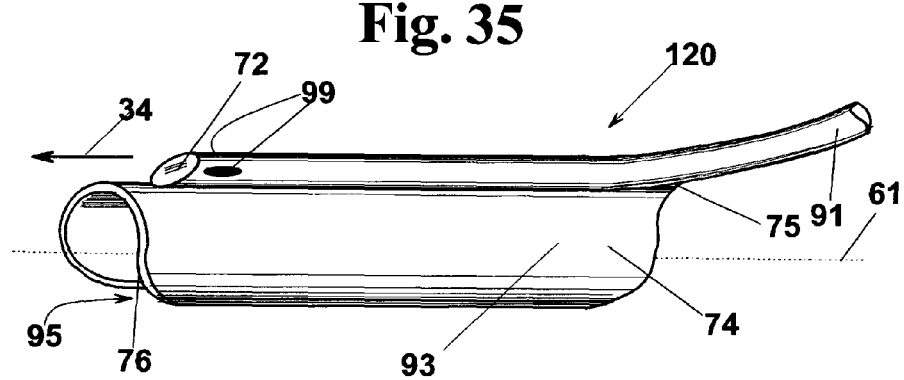
FIG. 35 shows a perspective view of a detail of an exemplary embodiment in alternative of the device of FIGS. 33 and 34.

With reference to FIG. 32, a device 100 is described according to a further exemplary embodiment of the invention, in which the contact preventing means for avoiding any contact between surgical glue 9 and biological medium 7 to be crossed for achieving operation region 4 comprises a liquid retaining means for keeping a barrier liquid 5 inside duct 41. Device 100 can be used for the haemostasis of entry site 2 of blood vessel 1, which is engaged by catheter introducer sheath 3. More in detail, device 100 comprises:

a syringe 51 that comprises a piston 44 and a cylinder 45, which define a container 103 where a dose of surgical glue 9 is arranged; cylinder 45 has a base 114 opposite to piston 44 with a through hollow tail portion 112, such that the outlet of glue 9 is possible, and the opposite base where a gripping portion 111 is mounted which assists handling of syringe 51, and provides a support to a protective cap 62;

a duct, in particular, a needle 41, which has an inlet port 42 and an outlet mouth 43, for conveying an outflow of surgical glue 9 between container 103 and operation region 4; piston 44 provides a pressurizing means for applying an injection pressure on surgical glue causing it to flow out of the duct. An amount of a barrier liquid 5, for example a saline solution, is arranged inside needle 41, and is contained between seals, not shown, which close outlet mouth 43 and inlet port 42 of duct 41. In particular, the seal of outlet mouth 43 can be manually removed, whereas the seal of inlet port 42 is broken by inserting needle 41 into tail portion 112. Piston 44 has a portion, for example the sealing portion 110, which offers an abutment to a locking means 79 that is fixed inside cylinder 45, therefore piston 44 cannot be withdrawn beyond a predetermined starting position. This way, saline solution 5 cannot flow back up in the duct due to the advancing movement through tissues 7 and under the blood pressure, in particular, the arterial pressure, allowing an operator to position device 100 with its outlet mouth 43 in an operation region 106, by pushing gripping portion 111 or cap 62, without contact of the blood with the surgical glue before and during the initial releasing step; the surgical glue is then released by pushing piston 44, and reaches operation region 106 substantially undiluted. In alternative to locking means 79, to avoid backflow of barrier liquid 5, a seal can be provided, not shown, which closes the hole of tail portion 112, and which is broken when surgical glue 9, which is contained in container 103, receives an injection pressure P2, by pushing piston 44;

FIGS. 33 to 35 are partial perspective views of a device 120 according to another exemplary embodiment of the invention, in which the use of a barrier liquid, which is enclosed in a duct 91, is still provided for avoiding the contact of the surgical glue with the biological means, and in which a coupling means with an introducer sheath 3 is provided coaxially to duct 91, which has a substantially cylindrical short tube 93 that slides along introducer sheath 3. Device 120 comprises, furthermore, a syringe 51 (FIG. 32), and duct 91 has two seals that closes an inlet port, not shown, and an outlet mouth 99 for retaining the barrier liquid.

In particular, the seal of the inlet port is broken by inserting tail portion 112 of syringe 51 (FIG. 32) into the inlet port, thus obtaining an outer seal, for example by a means of luer-lock fittings. Similarly to the case shown in FIG. 32, barrier liquid 5, which is contained inside duct 41, comes into contact with surgical glue 9 that is present in container 103, however only a slight mixing may occur due to the small size of the interface that is created between the two liquids and to the short time that is left between the break of the seal of the inlet port 92 and the release of surgical glue 9 in operation region 4.

Furthermore, short tube 93 (FIG. 34) may have a longitudinal cut 95 along one of its generatrices that is located opposite to the duct 93 with respect to the axis 61 of short tube 93. Longitudinal cut 95 allows the operator to clasp short tube 93 to introducer sheath 3 at the end of an percutaneous interventions, by simply aligning and compressing it onto introducer sheath 3 along cut 95.

Figure 36:
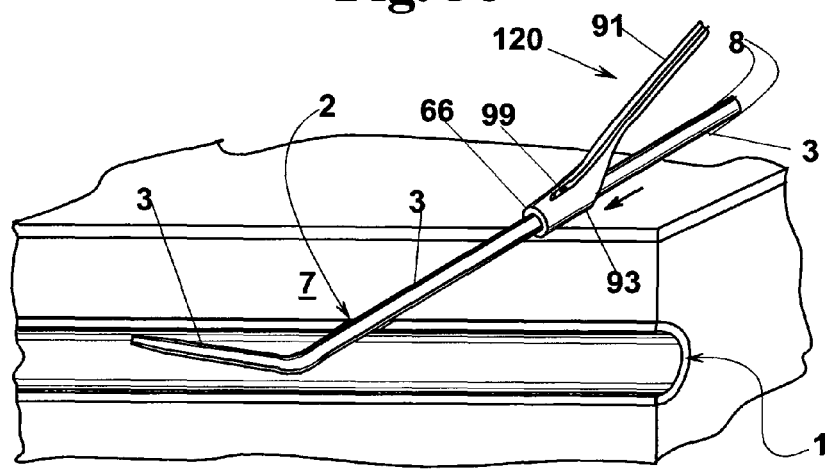
FIGS. 36 to 38 show a succession of closure operations of an arterial entry site by means of the device of FIGS. 33 and 34.

As shown in FIG. 36, the operator then causes short tube 93 to slide along the outer surface 8 of introducer sheath 3 by pushing with his hand on gripping portion 111 or on cap 62 of syringe 51 (FIG. 32). During the sliding movement, barrier liquid 5 is retained in duct 91: in fact, despite the arterial pressure, barrier liquid 5 cannot flow back towards cylinder 45 due to locking means 79 (FIG. 32), as already described. Furthermore, cap 62 prevents piston 44 from being accidentally operated.

Figure 37:
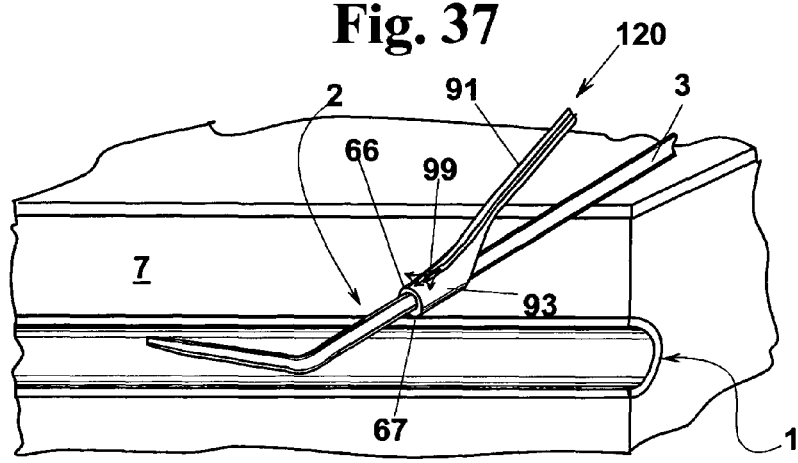
Figure 38:
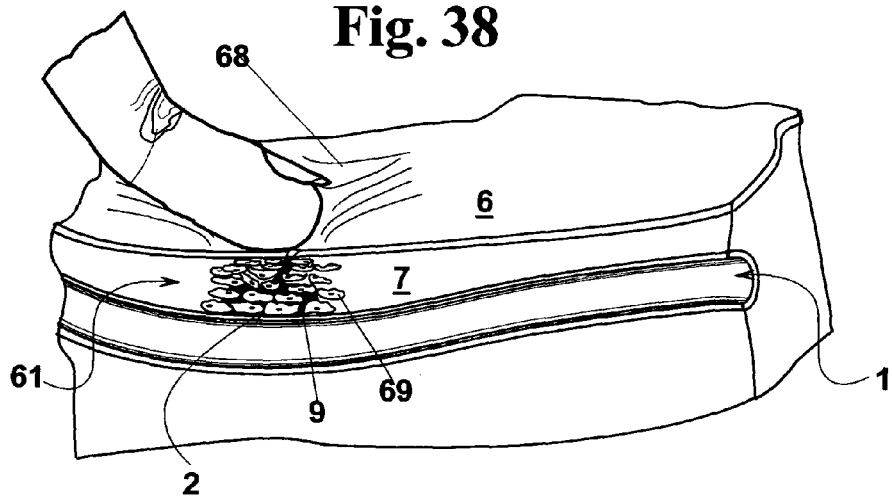
Figure 39:
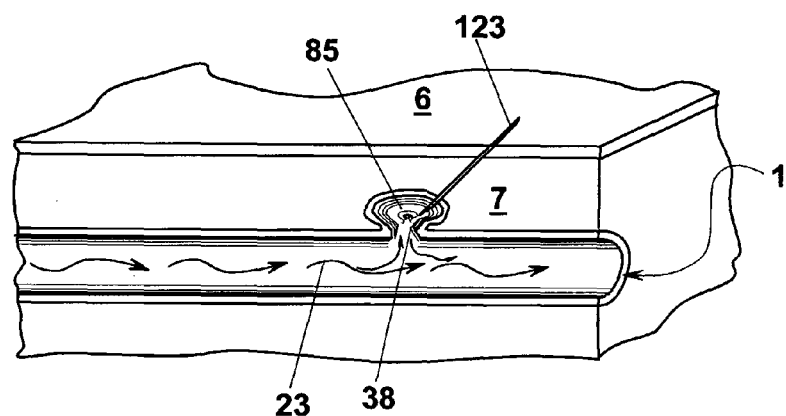
FIGS. 39 to 41 show diagrammatically a succession of treatment operations of a pseudoaneurysm directly connected to an artery, by means of the device of FIG. 32.
Figure 40:
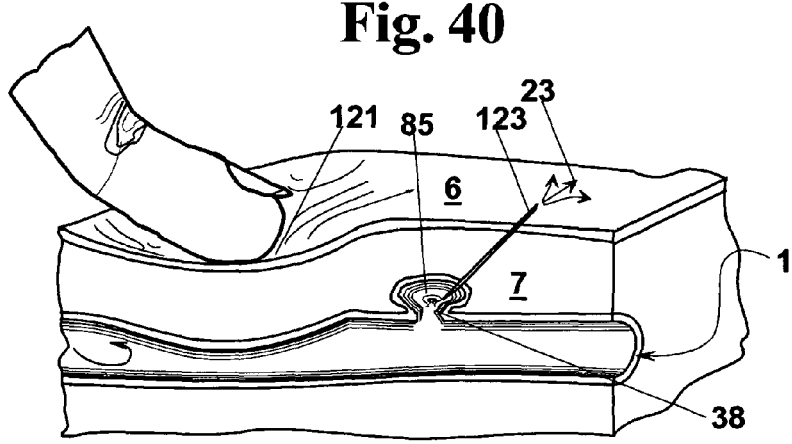
Figure 41:
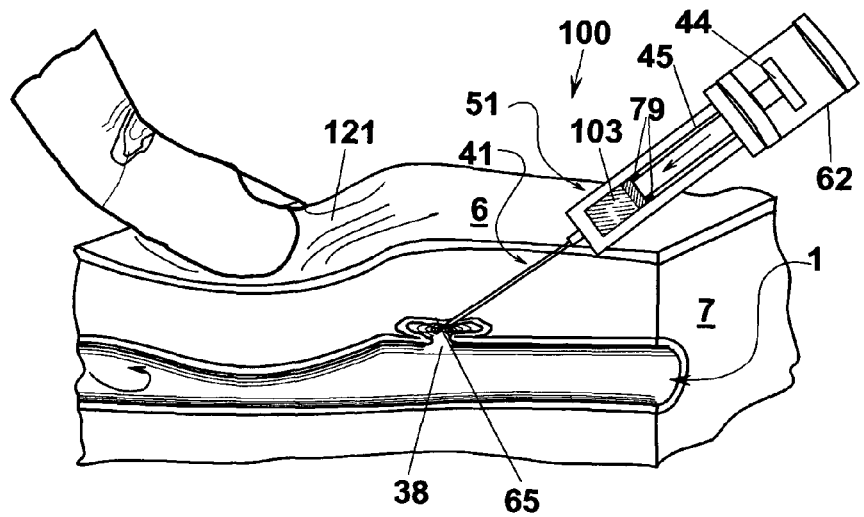
Figure 42:
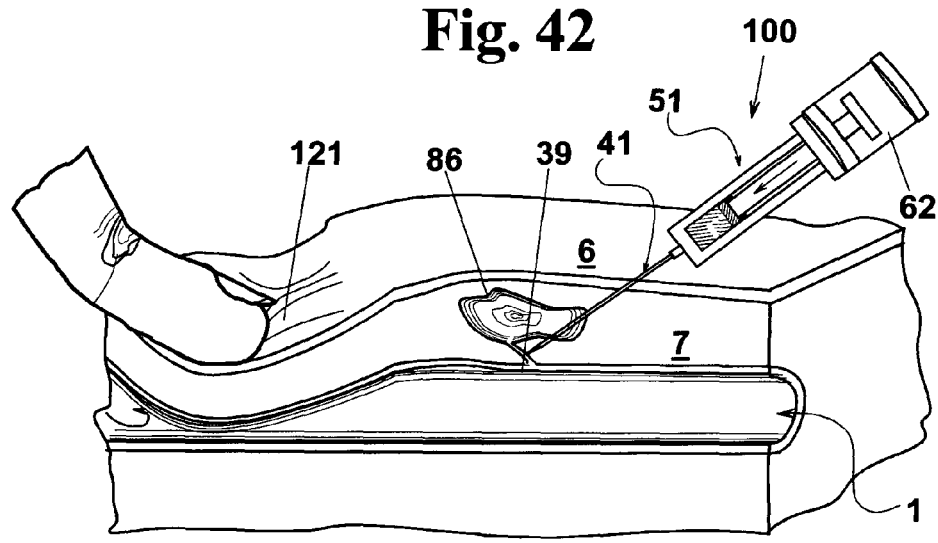
FIG. 42 diagrammatically shows a treatment of a pseudoaneurysm that is connected to an artery by a small duct by the device of FIG. 32.

Short tube 93 has a front surface 66, which abuts against the wall of artery 1 at a point 67 (FIG. 37) proximate to entry site 2. The position of outlet mouth 99 is then such that, when front surface 66 abuts upon blood vessel 1, the surgical glue which is expelled from outlet mouth 99 is released just before entry site 2. At the moment of the abutment, the operator stops sliding device 120 and pushes, advantageously with the same hand, on piston 44 for causing the outflow of the barrier liquid that is contained in duct 91 and then the outflow of surgical glue 9 through outlet mouth 99; at the end, the operator withdraws introducer sheath 3 and duct 91, and produces a manual compression 68 (FIG. 38) upon skin plane 6 above entry site 2, for some minutes. A matrix 61 is then formed which consists of surgical glue 9, blood, other liquid and tissues, in particular, fat 69; the matrix remains on the surface of blood vessel 1, and closes entry site 2. Surgical glue 9 seals furthermore, the channel left in tissues 7 that have been crossed by the introducer sheath, after its extraction.

Due to duct 91 integral to slide 93, the risks of releasing hardening material into blood vessel are limited, without any echographic control being needed.

Duct 91 has preferably a closed and tapered front end 72 (FIG. 33) in order to assist the movement of the duct through the tissues, according to the direction 34 towards entry site 2; similarly, front surface 66 of short tube 93 is rounded, i.e. it has a convexity 76, still according the direction 34, to prevent injuries to blood vessel 1 at the contact between short tube 93 and blood vessel 1. Outlet mouth 99 is laterally or above arranged on duct 91, thus limiting the risks of clotting due to tissues 7 that are crossed during the positioning movement of duct 91. Similarly, short tube 93 has a convexity 74, and a connection 75 with duct 91, to assist its extraction at the end of the haemostatic procedure.

With reference to FIGS. 39 to 42, the use of device 100 is described for treating a pseudoaneurysm 85 that is directly connected to an artery, or one 86 that is connected to an artery through a small duct (FIG. 42), i.e. formations that are defined by tissue 7 around blood vessel 1, and that pulsate due to the blood 23 (FIG. 39) that enters and exits through a direct passage 38, or a duct 39. In the case of a pseudoaneurysm that is directly connected to an artery 85, the procedure provides a compression 121 upon skin plane 6 above the blood vessel upstream with respect to pseudoaneurysm 85, and then a compression upon skin plane 6 above pseudoaneurysm 85 until pseudoaneurysm 85 is completely deflated and shrunk on the wall of blood vessel 1 (FIG. 42), after a needle 123 has been inserted which allows out blood 23 to flow out of the aneurysm to prevent the walls from being broken due to the compression. Afterwards, preferably under echographic control, device 100 is guided through tissues 7: since needle 41 is stably filled with saline solution, and piston 44 cannot be withdrawn, due to previously described locking means 79, or to an equivalent means, neither an inlet nor an early contact of blood or of other biological liquids may occur with the surgical glue, thus preventing solidification within needle 41 and blocking of device 100; for the same reason, the surgical glue is released in a pure state into shrunk pseudoaneurysm 85, where it reacts completely and creates a matrix with the tissues which is suitable for blocking the passage 78, without any dissolution of surgical glue into blood vessel 1 or through tissues 7. Compression 121 upon skin plane 6 is then interrupted, and what remains of pseudoaneurysm 85 is subsequently naturally reabsorbed.

Similarly, in case of pseudoaneurysm 86 that is connected to an artery by a small duct (FIG. 42), the procedure provides a compression 121 for blocking blood supply through the duct 39; preferably, a dose of surgical glue is released in duct 39 for definitively clogging it; pseudoaneurysm 86 is then aspirated percutaneously, and what remains of the tumefaction, which is no longer supplied with blood, is left free, and is subsequently naturally reabsorbed. In this case is much clearer as the surgical glue would react quantitatively in duct 39 or in aneurysm 86, to avoid that enters into blood vessel 1 and hardens embolizing remote vascular zones; this is possible if the particularly reactive surgical glue achieves substantially pure the zone of the operation, which is made possible by the device according to the invention.

Figure 43:
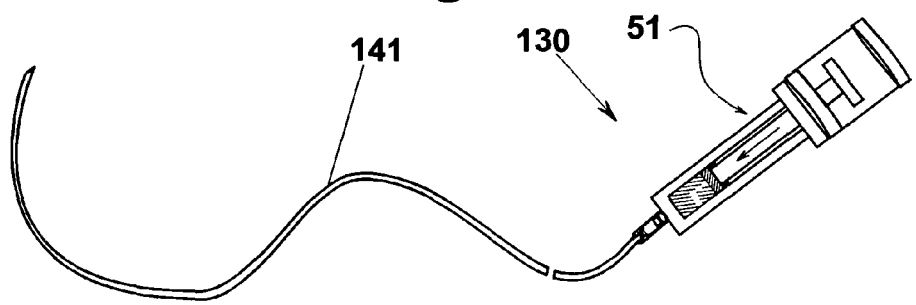
FIGS. 43 and 44 show diagrammatically an embolization of a blood vessel by a device according to a further exemplary embodiment of the invention, in which the duct is a catheter adapted to move along an endovascular path in a patient.
Figure 44:
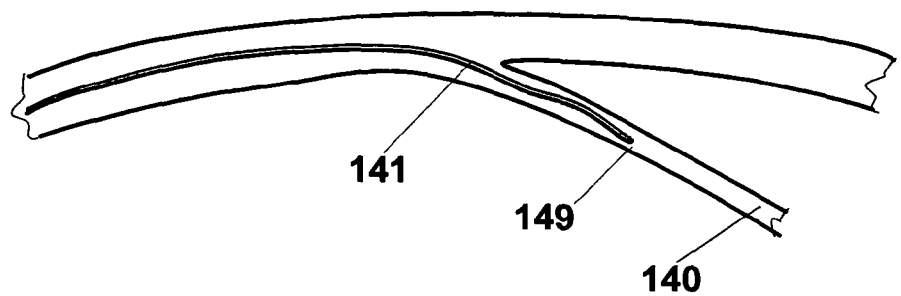

With reference to FIGS. 43 and 44, a device 130 is shown according to an exemplary embodiment of the invention in which the duct 141 is a catheter filled with a barrier liquid. Catheter 141 is adapted to move through the blood vessels, under echographic or radiographic control, for achieving with an outlet mouth 149 an endovascular operation region, in particular, a section of a blood vessel 140 to be embolized. Device 130 may comprise, for example, a syringe 51, which comprises a reservoir for surgical glue, as well as a pressurizing means for applying an injection pressure on such surgical glue. As in the case of the treatment of the pseudoaneurysm of FIG. 42, the surgical glue must react exclusively in the operation region of blood vessel 140, to prevent hardening material from being washed away by the blood stream and from being spread in remote vascular districts, with the consequent risks. The amount of barrier liquid is defined by the volume contained in catheter 141 between the entry site through the skin of the patient, not shown, and the operation region of blood vessel 140.

Figure 45:
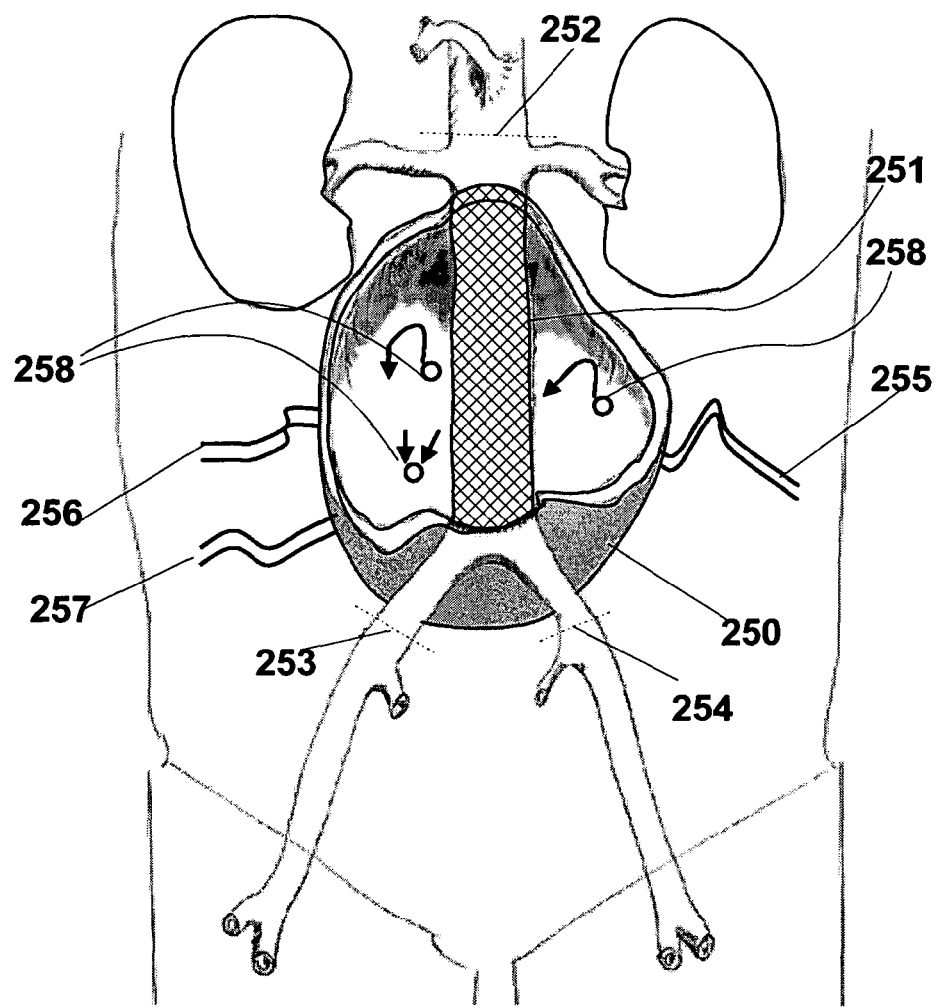
FIG. 45 diagrammatically shows a treatment of an endoleak after application of an endoprosthesis about an aneurysm.

FIG. 45 diagrammatically shows an endoleak that can be treated by the technique for treating an aneurysm 250. The technique provides tightly arranging an endoprosthesis 251 about the aneurysm, such that a continuity is created between the sections 252, 253 and 254 of the blood vessels that are interested by aneurysm 250, and provides furthermore excluding aneurysm 250 from a direct blood flow. Inside aneurysm 250, however, the lumbar arteries s 255, 256, 257 remain pervious, and can maintain a flow of blood through aneurysm 250. This phenomenon is known as type II endoleak. In particular, arteries 255 and 256, in which blood pressure is higher than the internal pressure of aneurysm 250, change the normal direction of the blood flow and push the blood into aneurysm 250, whereas artery 257, which is at a lower pressure, drains this blood from aneurysm 250. This way, a pressure remains in the aneurysm, which may lead to bleeding. For eliminating the supply of blood by the lumbar arteries. it is possible, using the device according to the invention, to prick percutaneously aneurysm 250 and cause a quick setting surgical glue to reach the terminal of the lumbar arteries. A slow setting glue would be immediately drained by lumbar artery, and would cause an embolization with subsequent medullary ischemia or an ischemia of the muscular districts to which blood is distributed. With the device according to the invention, it is possible to bring a quick setting glue, for example a cyanoacrylic glue, to the terminals 258 in a pure state, substantially maintaining its reactivity, such that the glue completely reacts in the operation region without the phenomena of dissolution above described may take place.

Figure 46:
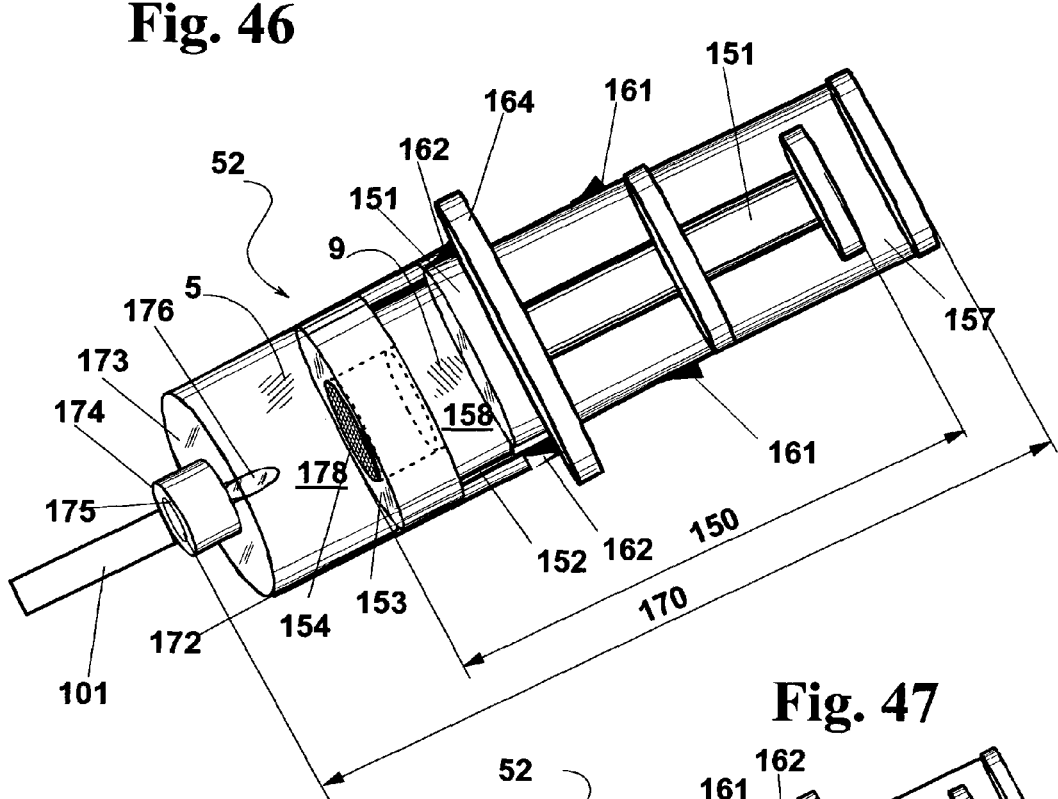
FIG. 46 shows a double syringe according to the invention, which is in alternative to the syringe shown in FIGS. 32, 41 and 42.

An exemplary embodiment 140 of devices 100, 120 and 130 comprises a double syringe 52 and any ducts selected from the group comprised of ducts 41,91,141, or any other which is adapted to retain a barrier liquid. This exemplary embodiment is shown in FIG. 46, with the detail of double syringe 52. Double syringe 52 comprises an internal syringe 150 and an external syringe 170. Internal syringe 150 comprises a piston 151 that one-way fluid tightly slides within a cylinder 152, which has a base 153 with a frangible portion 154 opposite to piston 151. External syringe 170 comprises a cylinder 172; internal syringe 150, which one-way fluid tightly slides within cylinder 172, works as the piston of external syringe 170. A protection cap 157 is provided which prevents contact with piston 151, for sliding internal syringe 150 within cylinder 172, and for avoiding at the same time accidental operation of piston 151 of syringe 150 itself. Preferably, cap 157 is pushed within cylinder 172 by arranging the thumb of a hand on cap 157, and other two fingers of the same hand opposite to a gripping portion 164, and then pushing the thumb towards the other two fingers that do not substantially move. The base 173 of cylinder 172, which is opposite to internal syringe 150, has a tail portion 174 that can be engaged with the inlet port of the duct of the device, not shown; tail portion 174 has a through hole 175, which allows the liquid to be conveyed through cylinder 172 of the duct, and a tip member 176 oriented towards the inside of cylinder 172, the tip member adapted to break frangible portion 154 when base 153 of cylinder 151 approaches base 173 of cylinder 172, during a sliding movement of syringe 150 within cylinder 172 towards its base 173. Advantageously, tip member 176 crosses tail portion 174, and contains the through hole 175.

Internal syringe 150, i.e. a portion of cylinder 152 that is not engaged by piston 151, provides a container 158 for surgical glue 9, and piston 151 provides a pressurizing means for applying an injection pressure on surgical glue 9, in order to cause it to flow out of cylinder 152. External syringe 170, i.e. a portion of cylinder 172 that is not engaged by syringe 150, provides a receptacle 178 for barrier liquid 5, and syringe 150, which can be manoeuvred as one piece as a piston by means of 157, provides a liquid outflow means for causing barrier liquid to flow out of cylinder 172, which can be operated independently from the pressurizing means. Frangible portion 154 keeps the surgical glue and the barrier liquid separated from each other in respective containers, before their use.

Figure 48:
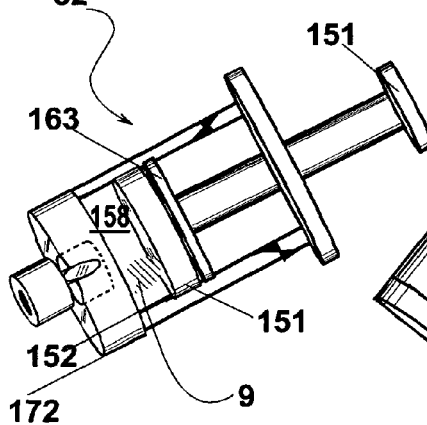
FIGS. 47 to 49 show the operation of the double syringe of FIG. 46.
Figure 47:
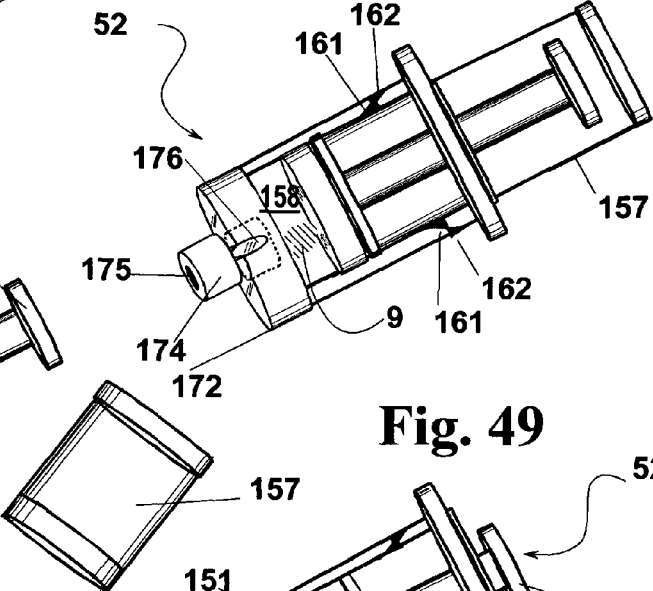

Double syringe 52 comprises couples of locking teeth 161/162, which operate at the end of a sliding movement of syringe 150 within cylinder 172, blocking syringe 150 in the final position, in which receptacle 178 of the barrier liquid is substantially empty. Furthermore, a block 163 (FIGS. 47-49) is provided, similar to block 79 of syringe 51, which prevents piston 151 from being withdrawn with respect to a predetermined starting position, moving away from base 153.

Referring to FIGS. 46-49, the operation is now described of a device comprising double syringe 52 and a duct like a needle 41 (FIGS. 32, 41 and 42), a duct 91 that is slidingly coupled with an introducer sheath 3 by means of a short tube (FIGS. 36 and 37), or a catheter 141 for percutaneous endovascular intervention (FIGS. 43 and 44). The device has a dose of surgical glue 9 that is available in container 158, and an amount of barrier liquid 5, for example a saline solution, in receptacle 178 (FIG. 46).

After hermetically connecting the duct of the device, not shown, with tail portion 174 (FIG. 46), an operator presses on cap 157 to cause internal syringe 150 to slide within cylinder 152 (FIGS. 46 and 47), which reduces the volume of receptacle 178 and causes saline solution to flow from receptacle 178 through hole 175 into the duct that is connected with tail portion 174. The amount of saline solution is enough to fill a portion of the duct or the whole duct according to specific requirements; receptacle 178 may have a normalized starting capacity, which is enough to fill with barrier liquid ducts that have a length suitable for reaching said remote operation regions through an endovascular path.

When receptacle 178 has been substantially emptied, i.e. at the end of an advancing movement of syringe 150 within cylinder 152, an interference is created between tip member 176 and frangible seal 154 that is broken bringing receptacle 158, which contains the surgical glue, in communication with the duct. Substantially at the same time of the break of frangible seal 154, locking teeth 161 that are integral to syringe 150 engage respective locking teeth 162 of cylinder 152 blocking the relative position of internal syringe 150 and of cylinder 152 in the final position. This way, syringe 150 cannot be withdrawn within cylinder 172 with respect to this position, and barrier liquid 5, which fills the duct, cannot flow either forwards or backwards; furthermore, the block of the starting position of internal piston 151 prevents a saline solution 5, which has come into contact with surgical glue 9 after break of frangible portion 154, from flowing back up into container 158 under the blood pressure.

Furthermore, the hermetic connection between duct 41, 91 or 141 and tail portion 174 prevents any air inlet, therefore barrier liquid 5 is retained within the duct.

Therefore, the operator can easily position the duct until outlet mouth 43 or 99 reaches the operation region, where surgical glue 9 must be released, without the blood back pressure that is encountered while moving through the blood vessel (in case of an endovascular intervention) causing internal syringe 150 to move back, blood to flow back up through the duct. Thanks to protection cap 157, the positioning of the duct in the patient's body is carried out without any risk of accidentally operating piston 151, i.e. without any risk of early releasing surgical glue 9.

Figure 49:
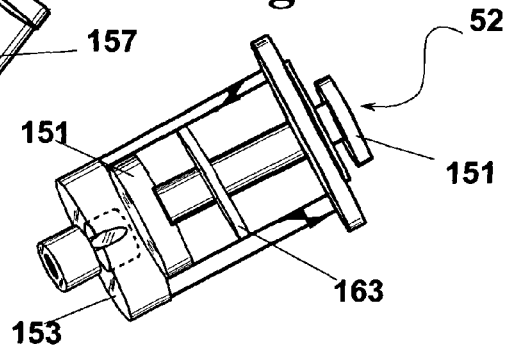

Once achieved the operation region, the operator removes cap 157 (FIG. 48) and acts on piston 151, causing surgical glue 9 to flow from container 158 into duct 41, 91 or 141. Then the operator may cause outflow of surgical glue 9 after barrier liquid 5 through the duct, by pushing piston 51 towards base 173 of cylinder 172 (FIG. 49).

The foregoing description of specific embodiments will so fully reveal the invention according to the conceptual point of view, so that others, by applying current knowledge, will be able to modify and/or adapt for various applications such embodiments without further research and without parting from the invention, and it is therefore to be understood that such adaptations and modifications will have to be considered as equivalent to the specific embodiments. The means and the materials to realise the different functions described herein could have a different nature without, for this reason, departing from the field of the invention. It is to be understood that the phraseology or terminology employed herein is for the purpose of description and not of limitation.

The invention claimed is:

1. A surgical glue-releasing device for closing a blood passage of a blood vessel in an operation region in a patient's body, wherein said operation region is located just before said blood passage, the device comprising an injection duct that has an inlet port and an outlet mouth arranged for releasing a surgical glue at said operation region, said injection duct being arranged to move through a biological medium in the patient's body from an opening on a skin plane of said patient to said operation region in such a way that, once said operation region has been reached by said injection duct, said outlet mouth is in said operation region and said inlet port remains outside of said opening on said skin plane, said inlet port is configured to be hydraulically connected with a source of said surgical glue and with a piston that can be operated by an operator for applying an injection pressure on said surgical glue and for causing:

flow of said surgical glue through said injection duct, and
a release of said surgical glue at said operation region through said outlet mouth,
wherein said outlet mouth is arranged against an outer surface of an introducer sheath, and said outlet mouth is configured to detach from said introducer sheath only when said piston is operated, in such a way to provide a one-way fluid tight contact against said outer surface of said introducer sheath and to impede a material of said biological medium from penetrating into said injection duct, thus preventing in said injection duct said surgical glue from contacting said biological medium before said surgical glue is released at said operation region through said outlet mouth.

2. A device according to claim 1, wherein said injection duct is arranged to be slidably coupled with said introducer sheath by a slide portion of said injection duct that is associated with a driving portion of said introducer sheath.

3. A device according to claim 1, wherein a short tube is provided that is arranged integrally with said duct and arranged to be coaxially coupled with said introducer sheath.

4. A device according to claim 3, wherein said outlet mouth and said short tube are such that said surgical glue is released in an annular narrow space that is defined between said short tube and said introducer sheath, such that said surgical glue reaches said operation region through said annular narrow space.

5. A device according to claim 4, comprising a seal ring at a rear end of said short tube, said rear end arranged, in use, proximate to said skin plane, said seal ring being suitable for preventing the surgical glue from leaking through a corresponding rear end of said narrow space, said seal ring comprising, in particular, a sealing ring that is arranged inside said narrow space.

6. A device according to claim 3, wherein said short tube has a cut from a front end of said short tube, said front end oriented in use towards said operation region, to a rear end of said short tube, such that by closely aligning and reciprocally compressing said short tube and said introducer sheath, said short tube forms a snap fit with said introducer sheath and a sliding coupling is obtained between said short tube and said introducer sheath.

7. A device according to claim 1, wherein an abutment is provided for blocking a movement of said injection duct with respect to said introducer sheath.

8. A device according to claim 7, wherein said abutment is integral to said injection duct at a distance from said outlet mouth such that said outlet mouth is located at said distance from said skin plane when said abutment abuts against said skin plane.

9. A device according to claim 7, wherein said abutment is arranged to abut against a wall of said blood vessel at an entry site, and said outlet mouth is arranged at a predetermined distance from said abutment, in order to make an operator aware that said outlet mouth of said injection duct is ready for releasing said surgical glue proximate to said entry site.

10. A surgical glue-releasing device for closing a blood passage of a blood vessel in an operation region in a patient's body, wherein said operation region is located just before said blood passage, the device comprising an injection duct that has an inlet port and an outlet mouth which is arranged for releasing a surgical glue of quick-setting type at said operation region, said injection duct arranged to move through a biological medium in the patient's body from an opening on a skin plane of said patient to said operation region in such a way that, once said operation region has been reached by said duct, said outlet mouth is in said operation region and said inlet port remains outside of said opening on said skin plane, said inlet port configured to be hydraulically connected with a source of said surgical glue and with a piston that can be operated by an operator for applying an injection pressure on said surgical glue and for causing:
 a flow of said surgical glue through said injection duct, and
 a release of said surgical glue at said operation region through said outlet mouth,
 wherein a check valve is arranged at said outlet mouth, said check valve comprising a fixed part that is fixed with respect to said injection duct and a movable part that is movable with respect to said fixed part, wherein, when said piston is operated, said movable part is configured to change its position from:
 a closed position, in which said release of surgical glue is hindered, to
 an open position, in which said injection pressure causes said release of surgical glue at said operation region, in order to impede in said injection duct said surgical glue from contacting said biological medium before said surgical glue is released at said operation region through said outlet mouth, and to prevent a material of said biological medium from penetrating into said injection duct.

11. A device according to claim 10, wherein said injection duct is arranged to be coupled with an elongated introducer sheath that can extend between said opening on said skin plane and a vascular entry site, said introducer sheath having an outer surface, and is adapted to be engaged with said outer surface of said introducer sheath.

12. A device according to claim 11, wherein said injection duct is arranged to be slidably coupled with said introducer sheath by a slide portion of said injection duct that is associated with a driving portion of said introducer sheath.

13. A device according to claim 11, wherein a short tube is provided that is arranged integral to said duct and is arranged to be coaxially coupled with said elongated introducer sheath.

14. A surgical glue-releasing device for closing a blood passage of a blood vessel in an operation region in a patient's body, wherein said operation region is located just before said blood passage, the device comprising an injection duct that has an inlet port and an outlet mouth which is arranged for releasing a surgical glue at said operation region, said injection duct arranged to move through a biological medium in the patient's body from an opening on a skin plane of said patient to said operation region in such a way that, once said operation region has been reached by said duct, said outlet mouth is in said operation region and said inlet port remains outside of said opening on said skin plane, said inlet port configured to be hydraulically connected with a source of said surgical glue and with a piston that can be operated by an operator for applying an injection pressure on said surgical glue and for causing:
 a flow of said surgical glue through said injection duct, and
 a release of said surgical glue at said operation region through said outlet mouth,
 wherein said injection duct is configured for retaining a barrier liquid,
 wherein an outflow actuator is provided that can be operated by said operator for causing an outflow of said barrier liquid through said injection duct, in such a way that:
 said barrier liquid interposes between said surgical glue and said outlet mouth, and
 by operating said outflow actuator and said piston, said barrier liquid flows out of said outlet mouth before said surgical glue is released at said outlet mouth, in such a way that said surgical glue is substantially undiluted when it is released at said operation region, in order to impede in said injection duct said surgical glue from contacting said biological medium before said surgical glue is released at said operation region through said outlet mouth.

15. A device according to claim 14, comprising a container for said barrier liquid, said container selected from the group consisting of:
 a portion of said injection duct; and
 a receptacle that in use is hydraulically connected to said injection duct.

16. A device according to claim 15, wherein said container contains said barrier liquid selected from the group consisting of:
 a saline solution;
 a glucose solution;
 distilled water; and
 a liquid contrast agent.

17. A device according to claim 15, wherein a seal is provided for isolating said barrier liquid in said container, wherein said seal can be removed or broken by at least one action selected from the group consisting of:
 operating said outflow actuator;
 operating said piston; and
 connecting said injection duct with said container of said barrier liquid.

18. A device according to claim 15, comprising a double syringe which comprises:
 an internal syringe that comprises said piston that one-way fluid-tightly slides inside a first cylinder, said first cylinder having a base with a portion that comprises a frangible seal and is opposite to said piston;
 an external syringe that comprises a second cylinder and said internal syringe that one-way fluid tightly slides in said second cylinder, said second cylinder having a base that is opposite to said internal syringe with a tail portion, said tail portion having an outlet hole, and a tip member that is oriented towards the inside of said second cylinder and is arranged to break said frangible seal when said base of said first cylinder approaches said base of said second cylinder, wherein said internal syringe provides said receptacle for said surgical glue, wherein said external syringe provides said receptacle for said barrier liquid and said outflow actuator which can be operated independently from said piston, wherein locking teeth integral to said internal syringe are arranged to engage with respective locking teeth integral to said second cylinder, so as to mechanically lock said internal syringe at a final position within said second cylinder, wherein a protrusion is provided fixed inside said first cylinder arranged to abut against a portion of said piston, so as to lock said piston at a predetermined starting position within said first cylinder, and wherein a cap is provided which is releasably connected with said first cylinder for avoiding accidental operation of said piston.

19. A device according to claim 14, wherein said outflow actuator is arranged to be operated independently from said piston.

20. A device according to claim 19, wherein a seal is arranged for avoiding accidental operation of said piston before said outflow of said barrier liquid.

21. A device according to claim 14, wherein said injection duct is arranged to be coupled with an elongated introducer sheath that can extend between said opening on said skin plane and a vascular entry site, said introducer sheath having an outer surface, and is adapted to be engaged with said outer surface of said introducer sheath.

22. A device according to claim 21, wherein said injection duct is arranged to be slidably coupled with said introducer sheath by a slide portion of said injection duct that is associated with a driving portion of said introducer sheath.

23. A device according to claim 21, wherein a short tube is provided that is arranged integral to said duct and is arranged to be coaxially coupled with said elongated introducer sheath.

* * * * *